(12) United States Patent
Hashimoto et al.

(10) Patent No.: US 10,809,619 B2
(45) Date of Patent: Oct. 20, 2020

(54) RESIST UNDERLAYER FILM-FORMING COMPOSITION CONTAINING SUBSTITUTED CROSSLINKABLE COMPOUND

(71) Applicant: NISSAN CHEMICAL INDUSTRIES, LTD., Tokyo (JP)

(72) Inventors: Keisuke Hashimoto, Toyama (JP); Kenji Takase, Toyama (JP); Tetsuya Shinjo, Toyama (JP); Rikimaru Sakamoto, Toyama (JP); Takafumi Endo, Toyama (JP); Hirokazu Nishimaki, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/900,384

(22) PCT Filed: Jun. 24, 2014

(86) PCT No.: PCT/JP2014/066680
§ 371 (c)(1),
(2) Date: Dec. 21, 2015

(87) PCT Pub. No.: WO2014/208542
PCT Pub. Date: Dec. 31, 2014

(65) Prior Publication Data
US 2016/0139509 A1    May 19, 2016

(30) Foreign Application Priority Data

Jun. 26, 2013 (JP) .................. 2013-134277
Jul. 22, 2013 (JP) .................. 2013-151934

(51) Int. Cl.
| | |
|---|---|
| *G03F 7/11* | (2006.01) |
| *C09D 161/22* | (2006.01) |
| *C09D 161/06* | (2006.01) |
| *C08G 12/08* | (2006.01) |
| *G03F 7/09* | (2006.01) |
| *G03F 7/40* | (2006.01) |
| *C07C 39/10* | (2006.01) |
| *C07C 43/178* | (2006.01) |
| *H01L 21/311* | (2006.01) |

(52) U.S. Cl.
CPC ............... *G03F 7/11* (2013.01); *C07C 39/10* (2013.01); *C07C 43/1785* (2013.01); *C08G 12/08* (2013.01); *C09D 161/06* (2013.01); *C09D 161/22* (2013.01); *G03F 7/091* (2013.01); *G03F 7/094* (2013.01); *G03F 7/40* (2013.01); *H01L 21/31138* (2013.01); *H01L 21/31144* (2013.01)

(58) Field of Classification Search
CPC . G03F 7/091; G03F 7/095; G03F 7/11; G03F 7/094; C07C 39/10; C07C 43/1785; C08G 12/08; C09D 161/06; C09D 161/22; H01L 21/31138; H01L 21/31144
See application file for complete search history.

(56) References Cited

U.S. PATENT DOCUMENTS

| | | | | |
|---|---|---|---|---|
| 6,083,658 A * | 7/2000 | Kunita | .................. | G03F 7/0045 430/270.1 |
| 6,132,935 A * | 10/2000 | Kobayashi | ............ | B41C 1/1008 430/270.1 |

(Continued)

FOREIGN PATENT DOCUMENTS

| | | |
|---|---|---|
| JP | H11-160860 A | 6/1999 |
| JP | 2003-122006 A | 4/2003 |

(Continued)

OTHER PUBLICATIONS

English translation of JP, 2008-308572, A (2008) from machine translation from AIPN Japan Patent Office National Center for Industrial Property Information and Training, generated Apr. 14, 2016, 10 pages.*

(Continued)

*Primary Examiner* — Cynthia Hamilton
(74) *Attorney, Agent, or Firm* — Oliff PLC

(57) ABSTRACT

A resist underlayer film for use in lithography process which generates less sublimate, has excellent embeddability at the time of applying onto a substrate having a hole pattern, and has high dry etching resistance, wiggling resistance and heat resistance, etc. A resist underlayer film-forming composition including a resin and a crosslinkable compound of Formula (1) or Formula (2):

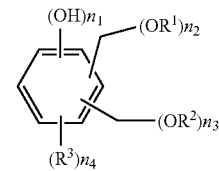

(1)

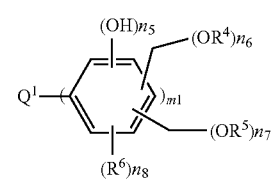

(2)

in which $Q^1$ is a single bond or an m1-valent organic group, $R^1$ and $R^4$ are each a $C_{2-10}$ alkyl group or a $C_{2-10}$ alkyl group having a $C_{1-10}$ alkoxy group, $R^2$ and $R^5$ are each a hydrogen atom or a methyl group, $R^3$ and $R^6$ are each a $C_{1-10}$ alkyl group or a $C_{6-40}$ aryl group.

12 Claims, 9 Drawing Sheets

(56) References Cited

U.S. PATENT DOCUMENTS

| | | | | |
|---|---|---|---|---|
| 6,511,783 B1* | 1/2003 | Uenishi | ............... | G03F 7/0045 |
| | | | | 430/270.1 |
| 6,514,656 B1* | 2/2003 | Nakamura | ............ | G03F 7/0045 |
| | | | | 430/270.1 |
| 8,715,916 B2* | 5/2014 | Minegishi | ................ | G03F 7/11 |
| | | | | 430/271.1 |
| 9,090,119 B2* | 7/2015 | Minegishi | ................ | G03F 7/11 |
| 2003/0124456 A1* | 7/2003 | Shirakawa | ............ | G03F 7/0045 |
| | | | | 430/270.1 |
| 2009/0280435 A1 | 11/2009 | McKenzie et al. | | |
| 2011/0251323 A1* | 10/2011 | Yoshimura | ............. | G03F 7/094 |
| | | | | 524/317 |
| 2011/0284855 A1* | 11/2011 | Miyoshi | ............. | H01L 51/5284 |
| | | | | 430/270.1 |
| 2012/0181251 A1* | 7/2012 | Minegishi | ................ | G03F 7/11 |
| | | | | 216/49 |

FOREIGN PATENT DOCUMENTS

| | | | |
|---|---|---|---|
| JP | 2007-529037 A | | 10/2007 |
| JP | 2008-308572 A | * | 12/2008 |
| JP | 2009175436 A | | 8/2009 |
| JP | 2010-237491 A | | 10/2010 |
| JP | 2011-520148 A | | 7/2011 |
| JP | 2012-515369 A | | 7/2012 |
| WO | 2005/089150 A2 | | 9/2005 |
| WO | 2008/143302 A1 | | 11/2008 |
| WO | 2010/083350 A1 | | 7/2010 |
| WO | 2010/147155 A1 | | 12/2010 |
| WO | 2011/040340 A1 | | 4/2011 |
| WO | WO 2014/126626 A1 | * | 2/2013 |

OTHER PUBLICATIONS

Dow, "Dowanol TM PM", Technical Data Sheet, 2 pages Dow Chemical Company published 2012. (Year: 2012).*

Sep. 16, 2014 Search Report issued in International Patent Application No. PCT/JP2014/066680.

Sep. 16, 2014 Written Opinion issued in International Patent Application No. PCT/JP2014/066680.

Uknown; "Lakokrasochnye Materialy i lkh Primeneie"; 1971; vol. 5; pp. 23-25.

* cited by examiner

RESIST UNDERLAYER FILM-FORMING COMPOSITION CONTAINING SUBSTITUTED CROSSLINKABLE COMPOUND

TECHNICAL FIELD

The present invention relates to a crosslinking catalyst for a resist underlayer film-forming composition for lithography that is effective at the time of semiconductor substrate processing, a resist underlayer film-forming composition containing the crosslinking catalyst, a method for forming a resist pattern using the resist underlayer film forming composition, and a method for producing a semiconductor device.

BACKGROUND ART

Conventionally, microfabrication has been carried out by lithography using a photoresist composition in the production of semiconductor devices. The microfabrication is a processing method including forming a thin film of a photoresist composition on a to-be-processed substrate such as a silicon wafer, irradiating the thin film with active light such as ultraviolet rays through a mask pattern in which a pattern of a semiconductor device is depicted, developing the pattern, and etching the to-be-processed substrate such as a silicon wafer by using the obtained photoresist pattern as a protection film. In recent years, however, semiconductor devices have been further integrated, and the active light to be used has had a shorter wavelength from a KrF excimer laser (248 nm) to an ArF excimer laser (193 nm). This raises serious problems of the effects of diffused reflection of active light from the substrate and standing wave. Consequently, a method has been widely applied in which a resist underlayer film called a bottom anti-reflective coating (BARC) is provided between a photoresist and a to-be-processed substrate.

In order to achieve further microfabrication, a lithography technique using extreme ultraviolet rays (EUV, wavelength 13.5 nm) and electron beams (EB) as the active light has been developed. In the EUV lithography or the EB lithography, a specific anti-reflective coating is not required because the diffused reflection from the substrate and the standing wave are not usually generated. The resist underlayer film, however, has begun to be widely studied as an auxiliary film for improving the resolution of a resist pattern and adhesion.

The resist underlayer film formed between the photoresist and the processed substrate is generally formed as a thermally curable crosslinking film that does not generate mixing with the resist through a baking process after the application of the resist underlayer film-forming composition onto the processed substrate in order to reduce mixing with the resist stacked on the upper layer.

Usually, a crosslinkable compound (a crosslinking agent) and a catalyst (a crosslinking catalyst) for promoting the crosslinking reaction are added to the resist underlayer film-forming composition in addition to a polymer resin being a main component in order to form such a thermally curable film. In particular, a thermal acid generator such as a sulfonic acid compound, a carboxylic acid compound, and a sulfonic acid ester is mainly used as the crosslinking catalyst.

In recent years, generation of a sublimation component (sublimate) derived from the polymer resin and low molecular weight compounds such as the crosslinking agent and the crosslinking catalyst at the time of baking when the resist underlayer film is formed by using the resist underlayer film-forming composition in the lithography process of semiconductor device production has been a new problem. Such sublimate contaminates the inside of film formation apparatus by attaching and accumulating the sublimate in the film formation apparatus during the semiconductor device production process. These contaminations may be a generation factor of defects and the like by attaching these contaminations onto wafers as foreign substances. Consequently, a new underlayer film-forming composition that can reduce the sublimate generated from the resist underlayer film as low as possible is required to be developed. A resist underlayer film showing a low sublimate generation property has been also studied (refer to, for example, Patent Document 1 and Patent Document 2).

In order to achieve excellent embeddability and reduce a sublimate amount, a technique of using a crosslinking agent having an N atom in a glycol urea-based compound and a melamine-based compound having a butyl ether group has been disclosed (refer to Patent Document 3).

In addition, a compound having hydroxymethyl group, methoxymethyl group, ethoxymethyl group, methoxypropoxymethyl group, or the like at the side chain has been disclosed (refer to Patent Document 4 and Patent Document 5).

PRIOR ART DOCUMENTS

Patent Documents

Patent Document 1: Japanese Patent Application Publication No. 2009-175436 (JP 2009-175436 A)
Patent Document 2: Japanese Patent Application Publication No. 2010-237491 (JP 2010-237491 A)
Patent Document 3: International Publication No, 2008/143302 Pamphlet (WO 2008/143302)
Patent Document 4: Japanese Patent Application Publication No. H11-160860 (JP H11-160860 A)
Patent Document 5: Japanese Patent Application Publication No. 2003-122006 (JP 2003-122006 A)

SUMMARY OF THE INVENTION

Problem to be Solved by the Invention

An object of the present invention is to provide a resist underlayer film-forming composition for use in a lithography process for a semiconductor device production.

The present invention provides a resist underlayer film-forming composition generating less sublimate and having excellent embeddability at the time of applying the composition onto a substrate having a hole pattern.

Means for Solving the Problem

The present invention provides, as a first aspect, a resist underlayer film-forming composition comprising a resin and a crosslinkable compound of Formula (1) or Formula (2):

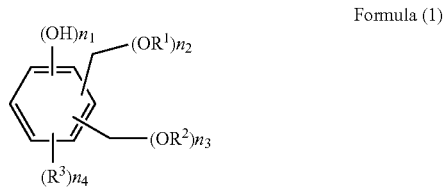

Formula (1)

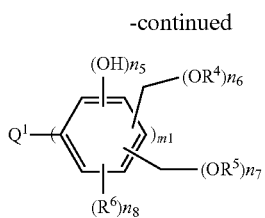

Formula (2)

(where $Q^1$ is a single bond or an m1-valent organic group; $R^1$ and $R^4$ are each a $C_{2-10}$ alkyl group or a $C_{2-10}$ alkyl group having a $C_{1-10}$ alkoxy group; $R^2$ and $R^5$ are each a hydrogen atom or a methyl group; $R^3$ and $R^6$ are each a $C_{1-10}$ alkyl group or a $C_{6-40}$ aryl group;

n1 is an integer of $1 \le n1 \le 3$; n2 is an integer of $2 \le n2 \le 5$; n3 is an integer of $0 \le n3 \le 3$; n4 is an integer of $0 \le n4 \le 3$; a total of the integers is an integer of $3 \le (n1+n2+n3+n4) \le 6$;

n5 is an integer of $1 \le n5 \le 3$; n6 is an integer of $1 \le n6 \le 4$; n7 is an integer of $0 \le n7 \le 3$; n8 is an integer of $0 \le n8 \le 3$; a total of the integers is an integer of $2 \le (n5+n6+n7+n8) \le 5$; and m1 is an integer of 2 to 10), as a second aspect, the resist underlayer film-forming composition according to the first aspect, in which $Q^1$ is a single bond or an m1-valent organic group selected from a $C_{1-10}$ chain hydrocarbon group, a $C_{6-40}$ aromatic group, or combination thereof, as a third aspect, the resist underlayer film-forming composition according to the first aspect or the second aspect, in which the crosslinkable compound of Formula (1) or Formula (2) is a compound obtained by reacting a compound of Formula (3) or Formula (4):

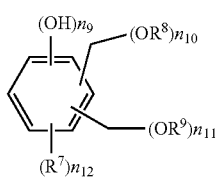

Formula (3)

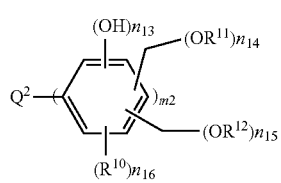

Formula (4)

(where $Q^2$ is a single bond or an m2-valent organic group; $R^8$, $R^9$, $R^{11}$, and $R^{12}$ are each a hydrogen atom or a methyl group; $R^7$ and $R^{10}$ are each a $C_{1-10}$ alkyl group or a $C_{6-40}$ aryl group;

n9 is an integer of $1 \le n9 \le 3$; n10 is an integer of $2 \le n10 \le 5$; n11 is an integer of $0 \le n11 \le 3$; n12 is an integer of $0 \le n12 \le 3$; a total of the integers is an integer of $3 \le (n9+n10+n11+n12) \le 6$;

n13 is an integer of $1 \le n13 \le 3$; n14 is an integer of $1 \le n14 \le 4$; n15 is an integer of $0 \le n15 \le 3$; n16 is an integer of $0 \le n16 \le 3$; a total of the integers is an integer of $2 \le (n13+n14+n15+n16) \le 5$; and m2 is an integer of 2 to 10) with an ether compound containing a hydroxy group or a $C_{2-10}$ alcohol, as a fourth aspect, the resist underlayer film-forming composition according to the third aspect, in which the reaction of the compound of Formula (3) or Formula (4) with the ether compound containing a hydroxy group or the $C_{2-10}$ alcohol is carried out in the presence of an acid catalyst, as a fifth aspect, the resist underlayer film-forming composition according to the fourth aspect, in which the acid catalyst is an ion-exchange resin, as a sixth aspect, the resist underlayer film-forming composition according to any one of the third aspect to the fifth aspect, in which the ether compound containing a hydroxy group is propylene glycol monomethyl ether or propylene glycol monoethyl ether, as a seventh aspect, the resist underlayer film-forming composition according to any one of the third aspect to the fifth aspect, in which the $C_{2-10}$ alcohol is ethanol, 1-propanol, 2-methyl-1-propanol, butanol, 2-methoxyethanol, or 2-ethoxyethanol, as an eighth aspect, the resist underlayer film-forming composition according to any one of the first aspect to the seventh aspect, in which the resin is a novolac resin, as a ninth aspect, the resist underlayer film-forming composition according to any one of the first aspect to the eighth aspect, further comprising a crosslinking agent, as a tenth aspect, the resist underlayer film-forming composition according to any one of the first aspect to the ninth aspect, further comprising an acid and/or an acid generator, as an eleventh aspect, a resist underlayer film obtained by applying the resist underlayer film-forming composition as described in any one of the first aspect to the tenth aspect onto a semiconductor substrate and baking the applied resist underlayer film-forming composition, as a twelfth aspect, a method for forming a resist pattern for use in semiconductor production, the method comprising: applying the resist underlayer film-forming composition as described in any one of the first aspect to the tenth aspect onto a semiconductor substrate, and baking the applied resist underlayer film forming composition to form a resist underlayer film, as a thirteenth aspect, a method for producing a semiconductor device, the method comprising: forming a resist underlayer film by using the resist underlayer film-forming composition as described in any one of the first aspect to the tenth aspect onto a semiconductor substrate; forming a resist film on the resist underlayer film; forming a resist pattern by irradiation with light or electron beams and development; etching the resist underlayer film by using the formed resist pattern; and processing the semiconductor substrate by using the patterned resist underlayer film, as a fourteenth aspect, a method for producing a semiconductor device, the method comprising: forming a resist underlayer film by using the resist underlayer film-forming composition as described in any one of the first aspect to the tenth aspect onto a semiconductor substrate; forming a hard mask on the resist underlayer film; forming a resist film on the hard mask; forming a resist pattern by irradiation with light or electron beams and development; etching the hard mask by using the formed resist pattern; etching the resist underlayer film by using the patterned hard mask; and processing the semiconductor substrate by using the patterned resist underlayer film, as a fifteenth aspect, the method according to the fourteenth aspect, in which the hard mask is formed by application of an inorganic substance or vapor-deposition of an inorganic substance, and as a sixteenth aspect, a compound of Formula (5):

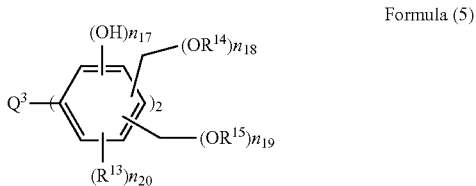

Formula (5)

(where $Q^3$ is an isopropylidene group; $R^{14}$ is a $C_{2-10}$ alkyl group or a $C_{2-10}$ alkyl group having a $C_{1-10}$ alkoxy group; $R^{15}$ is a hydrogen atom or a methyl group; $R^{13}$ is a $C_{1-10}$ alkyl group or a $C_{6-40}$ aryl group;

n17 is an integer of $1 \leq n17 \leq 3$; n18 is an integer of $1 \leq n18 \leq 4$; n19 is an integer of $0 \leq n19 \leq 3$; n20 is an integer of $0 \leq n20 \leq 3$; and a total of the integers is an integer of $2 \leq (n17+n18+n19+n20) \leq 5$).

Effects of the Invention

The crosslinkable compound used in the present invention is a crosslinkable compound obtained by substituting a $C_{2-10}$ long chain alkyl group or a $C_{2-10}$ alkyl group having a $C_{1-10}$ alkoxy group for an alkyl group part (for example, a low molecular weight alkyl group such as methyl group) in an alkoxy methyl group.

At the time of bonding the substituted crosslinkable compound with a resin to form a crosslink structure, an eliminated component eliminated from the crosslinkable compound is a compound having a large molecular weight corresponding to the alkyl group part. Consequently, it is considered that the components to be sublimated can be reduced when the resist underlayer film-forming composition containing the crosslinkable compound of the present invention was applied onto a substrate and the applied compound was heated. As described above, the sublimate attaches in the chamber and the attached sublimate is dropped onto the substrate to cause coating defects.

Consequently, the composition of the present invention in which the substituted crosslinkable compound is used allows the coating defects to be reduced.

The crosslinking reaction of the crosslinkable compound obtained by substituting the $C_{2-10}$ long chain alkyl group or the $C_{2-10}$ alkyl group having the C alkoxy group for the alkyl group part (for example, a low molecular weight alkyl group such as methyl group) in the alkoxy methyl group with the resin is moderately progressed. Consequently, after a fine hole pattern is covered with the resist underlayer film-forming composition containing the crosslinkable compound of the present invention, reduction in flowability associated with forming a three-dimensional structure caused by crosslink does not occur for some time. Consequently, use of the composition of the present invention allows the hole pattern to be filled with the resist underlayer film-forming composition without clearance gaps.

MODES FOR CARRYING OUT THE INVENTION

Figure 1:
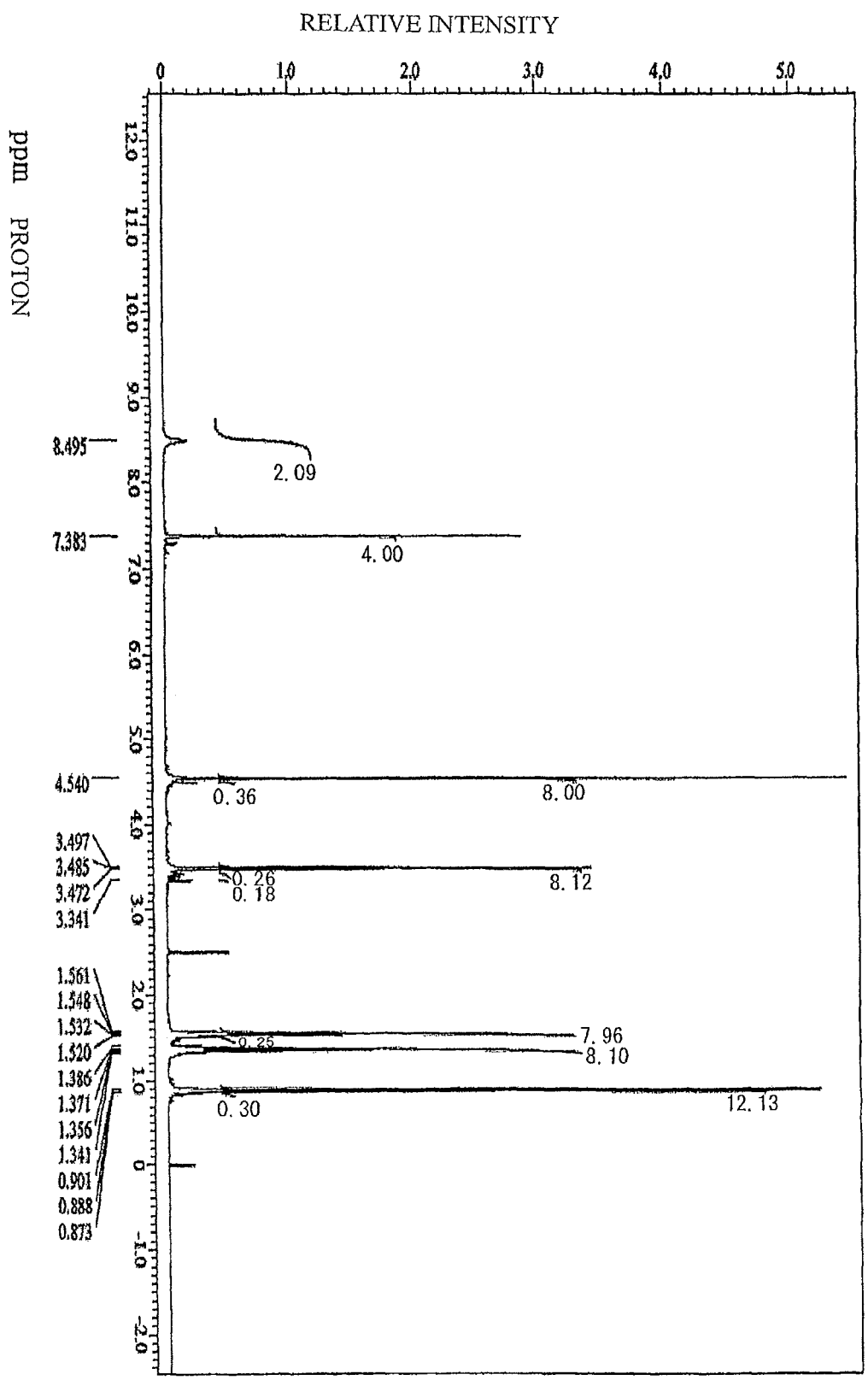
FIG. 1 is an NMR spectrum of the tetra-substituted compound of TBOM-BP-BU obtained in Synthesis Example 3.

The present invention relates to a resist underlayer film-forming composition containing a resin and a crosslinkable compound of Formula (1) and Formula (2).

The resist underlayer film-forming composition in the present invention usually contains a resin, a crosslinkable compound of Formula (1) or Formula (2), and a solvent. The resist underlayer film-forming composition may further contain additives such as an acid generator and a surfactant if necessary. The solid content in the composition is 0.1% by mass to 70% by mass or 0.1% by mass to 60% by mass. The solid content is a content ratio of the whole components of the resist underlayer film-forming composition from which the solvent is removed. In the solid content, the resin (polymer) can be contained in a ratio of 1% by mass to 99.9% by mass, 50% by mass to 99.9% by mass, 50% by mass to 95% by mass, or 50% by mass to 90% by mass.

In the solid content, the crosslinkable compound of Formula (1) or Formula (2) can be contained in a ratio of 0.01% by mass to 50% by mass, 0.01% by mass to 40% by mass, or 0.1% by mass to 30% by mass.

The polymer used in the present invention has a weight average molecular weight of 600 to 1,000,000 or 600 to 200,000.

In the crosslinkable compound of Formula (1) or Formula (2) used in the present invention, $Q^1$ is a single bond or an m1-valent organic group; $R^1$ and $R^4$ are each a $C_{2-10}$ alkyl group or a $C_{2-10}$ alkyl group having a $C_{1-10}$ alkoxy group; $R^2$ and $R^5$ are each a hydrogen atom or a methyl group; $R^3$ and $R^6$ are each a $C_{1-10}$ alkyl group or a $C_{6-40}$ aryl group.

n1 is an integer of $1 \leq n1 \leq 3$; n2 is an integer of $2 \leq n2 \leq 5$; n3 is an integer of $0 \leq n3 \leq 3$; n4 is an integer of $0 \leq n4 \leq 3$; and a total of the integers is an integer of $3 \leq (n1+n2+n3+n4) \leq 6$.

n5 is an integer of $1 \leq n5 \leq 3$; n6 is an integer of $1 \leq n6 \leq 4$; n7 is an integer of $0 \leq n7 \leq 3$; n8 is an integer of $0 \leq n8 \leq 3$; and a total of the integers is an integer of $2 \leq (n5+n6+n7+n8) \leq 5$. m1 is an integer of 2 to 10.

$Q^1$ is a single bond or an m1-valent organic group selected from a $C_{1-10}$ chain hydrocarbon group, a $C_{6-40}$ aromatic group, or a combination thereof. The chain hydrocarbon group may include the following alkyl groups. The aromatic group may include the following aryl groups.

Examples of the $C_{2-10}$ alkyl group may include ethyl group, n-propyl group, i-propyl group, cyclopropyl group, n-butyl group, i-butyl group, s-butyl group, t-butyl group, cyclobutyl group, 1-methyl-cyclopropyl group, 2-methyl-cyclopropyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, cyclopentyl group, 1-methyl-cyclobutyl group, 2-methyl-cyclobutyl group, 3-methyl-cyclobutyl group, 1,2-dimethyl-cyclopropyl group, 2,3-dimethyl-cyclopropyl group, 1-ethyl-cyclopropyl group, 2-ethyl-cyclopropyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, cyclohexyl group, 1-methyl-cyclopentyl group, 2-methyl-cyclopentyl group, 3-methyl-cyclopentyl group, 1-ethyl-cyclobutyl group, 2-ethyl-cyclobutyl group, 3-ethyl-cyclobutyl group, 1,2-dimethyl-cyclobutyl group, 1,3-dimethyl-cyclobutyl group, 2,2-dimethyl-cyclobutyl group, 2,3-dimethyl-cyclobutyl group, 2,4-dimethyl-cyclobutyl group, 3,3-dimethyl-cyclobutyl group, 1-n-propyl-cyclopropyl group, 2-n-propyl-cyclopropyl group, 1-i-propyl-cyclopropyl group, 2-i-propyl-cyclopropyl group, 1,2,2-trimethyl-cyclopropyl group, 1,2,3-trimethyl-cyclopropyl group, 2,2,3-trimethyl-cyclopropyl group, 1-ethyl-2-methyl-cyclopropyl group, 2-ethyl-1-methyl-cyclopropyl group, 2-ethyl-2-methyl-cyclopropyl group, and 2-ethyl-3-methyl-cyclopropyl group.

The $C_{1-10}$ alkyl group may include methyl group in addition to the $C_{2-10}$ alkyl group.

Examples of the $C_{1-10}$ alkoxy group may include methoxy group, ethoxy group, n-propoxy group, i-propoxy group, n-butoxy group, i-butoxy group, s-butoxy group, t-butoxy group, n-pentoxy group, 1-methyl-n-butoxy group, 2-methyl-n-butoxy group, 3-methyl-n-butoxy group, 1,1-dimethyl-n-propoxy group, 1,2-dimethyl-n-propoxy group, 2,2-dimethyl-n-propoxy group, 1-ethyl-n-propoxy group, n-hexyloxy group, 1-methyl-n-pentyloxy group, 2-methyl-n-pentyloxy group, 3-methyl-n-pentyloxy group, 4-methyl-n-pentyloxy group, 1,1-dimethyl-n-butoxy group, 1,2-dimethyl-n-butoxy group, 1,3-dimethyl-n-butoxy group, 2,2-dimethyl-n-butoxy group, 2,3-dimethyl n-butoxy group, 3,3-dimethyl-n-butoxy group, 1-ethyl-n-butoxy group, 2-ethyl-n-butoxy group, 1,1,2-trimethyl-n-propoxy group, 1,2,2-trimethyl-n-propoxy group, 1-ethyl-1-methyl-n-propoxy group, and 1-ethyl-2-methyl-n-propoxy group.

Examples of the $C_{6-40}$ aryl group may include phenyl group, naphthyl group, and anthryl group.

The crosslinkable compound of Formula (1) or Formula (2) can be obtained by reacting a compound of Formula (3) or Formula (4) with an ether compound containing a hydroxy group or a $C_{2-10}$ alcohol.

A compound of Formula (1) or Formula (2) formed by substituting the ether compound containing a hydroxy group or the $C_{2-10}$ alcohol for 1 mol of the compound of Formula (3) or Formula (4) in a ratio of 1 mol is determined as a mono-substituted compound. Similarly, a compound of Formula (1) or Formula (2) formed by substituting the ether compound containing a hydroxy group or the $C_{2-10}$ alcohol in a ratio of 2 mol is determined as a di-substituted compound. Similarly, a compound of Formula (1) or Formula (2) formed by substituting the ether compound containing a hydroxy group or the $C_{2-10}$ alcohol in a ratio of 3 mol is determined as a tri-substituted compound. Similarly, a compound of Formula (1) or Formula (2) formed by substituting the ether compound containing a hydroxy group or the $C_{2-10}$ alcohol in a ratio of 4 mol is determined as a tetra-substituted compound.

In Formula (3) and Formula (4), $Q^2$ is a single bond or an m2-valent organic group. More specifically, $Q^2$ can be the single bond or the m2-valent organic group selected from a $C_{1-10}$ chain hydrocarbon group, a $C_{6-40}$ aromatic group, or a combination thereof. Here, examples of the chain hydrocarbon group may include the alkyl group described above. Examples of the aromatic group may include the aryl group described above.

$R^8$, $R^9$, $R^{11}$, and $R^{12}$ are each a hydrogen atom or a methyl group and $R^7$ and $R^{10}$ are each a $C_{1-10}$ alkyl group or a $C_{6-40}$ aryl group.

n9 is an integer of $1 \leq n9 \leq 3$; n10 is an integer of $2 \leq n10 \leq 5$; n11 is an integer of $0 \leq n11 \leq 3$; n12 is an integer of $0 \leq n12 \leq 3$; and a total of the integers is an integer of $3 \leq (n9+n10+n11+n12) \leq 6$.

n13 is an integer of $1 \leq n13 \leq 3$; n14 is an integer of $1 \leq n14 \leq 4$; n15 is an integer of $0 \leq n15 \leq 3$; n16 is an integer of $0 \leq n16 \leq 3$; and a total of the integers is an integer of $2 \leq (n13+n14+n15+n16) \leq 5$. m2 is an integer of 2 to 10.

The reaction of the compound of Formula (3) or Formula (4) with the ether compound containing a hydroxy group or the $C_{2-10}$ alcohol is carried out in the presence of an acid catalyst.

Examples of the acid catalyst to be used may include acidic compounds such as p-toluenesulfonic acid, trifluoromethanesulfonic acid, pyridinium p-toluenesulfonate, salicylic acid, 5-sulfosalicylic acid, 4-phenolsulfonic acid, camphorsulfonic acid, 4-chlorobenzenesulfonic acid, benzenedisulfonic acid, 1-naphthalenesulfonic acid, citric acid, benzoic acid, hydroxybenzoic acid, and naphthalene carboxylic acid.

As the acid catalyst, an ion-exchange resin can be used in order not to leave an unreacted acid in the reaction system. Examples of the ion-exchange resin to be used may include a sulfonic acid-based strong acid ion-exchange resin.

Examples of the ether compound containing a hydroxy group may include propylene glycol monomethyl ether or propylene glycol monoethyl ether.

Examples of the $C_{2-10}$ alcohol may include ethanol, 1-propanol, 2-methyl-1-propanol, butanol, 2-methoxyethanol, or 2-ethoxyethanol.

The crosslinkable compound of Formula (1) or Formula (2) used in the present invention, for example, can be exemplified as follows:

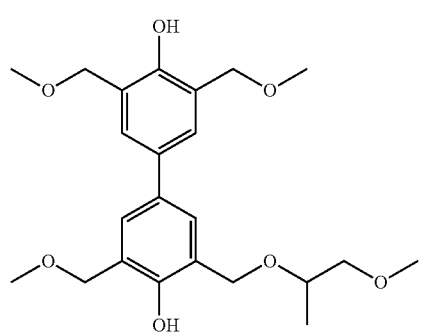

Formula (3-1)

Formula (3-2)
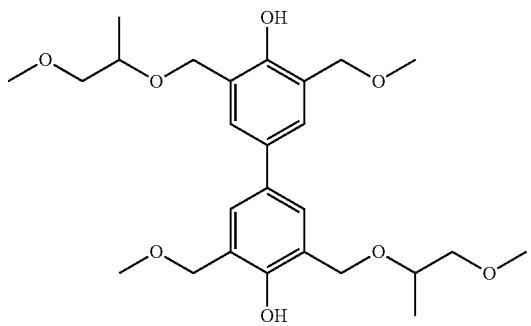
Formula (3-6)
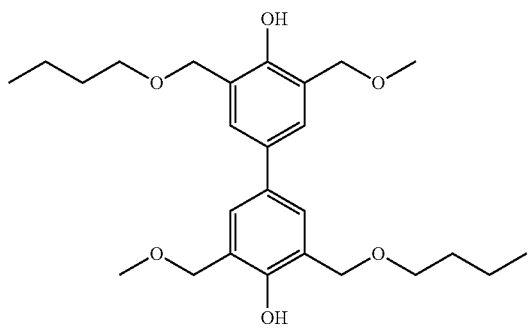
Formula (3-3)
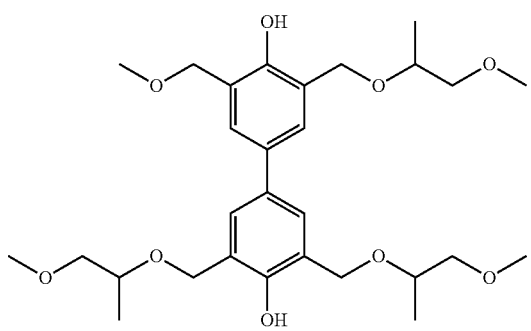
Formula (3-7)
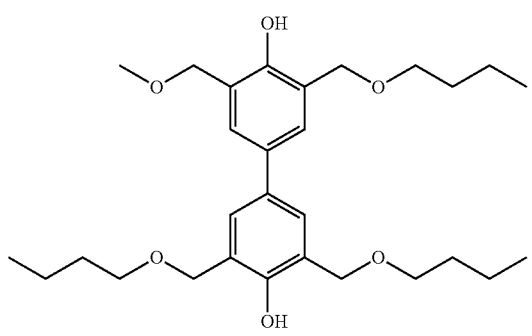
Formula (3-4)
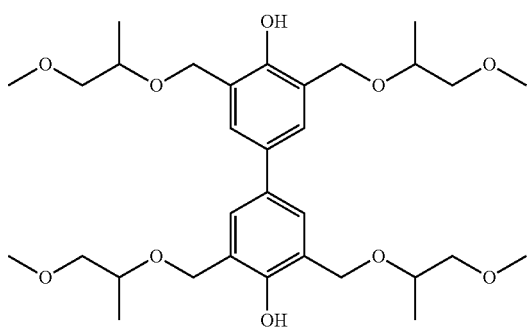
Formula (3-8)
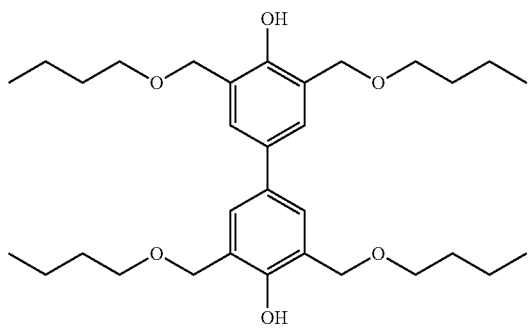
Formula (3-5)
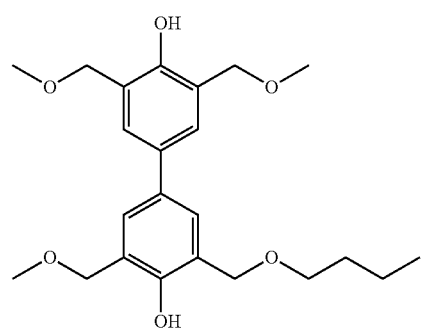
Formula (3-9)
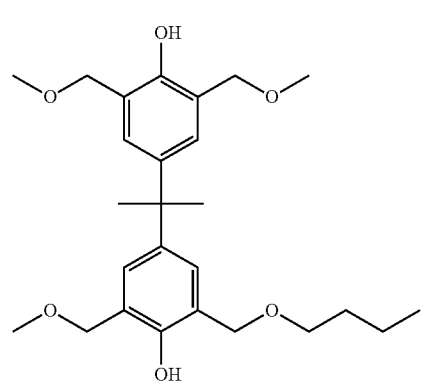

Formula (3-10)
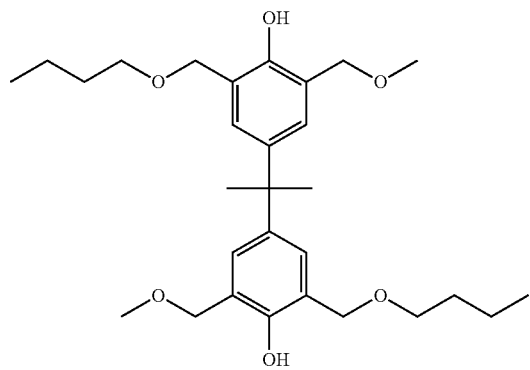
Formula (3-11)
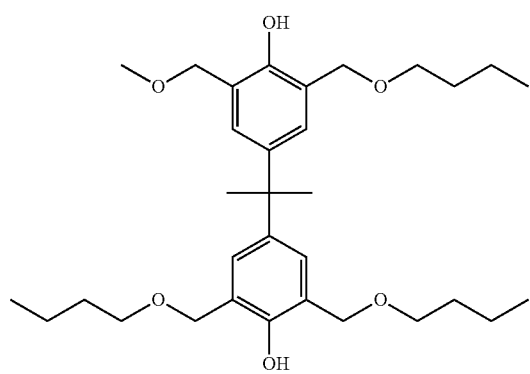
Formula (3-12)
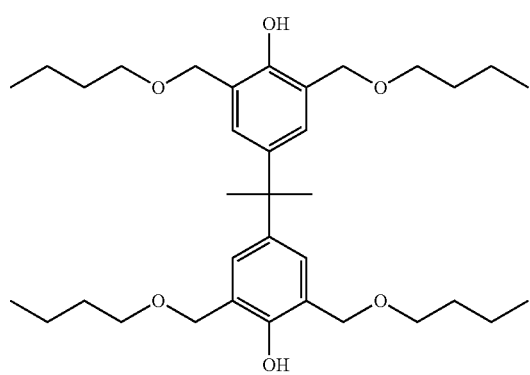
Formula (3-13)
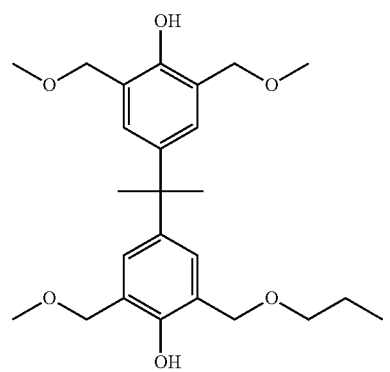
Formula (3-14)
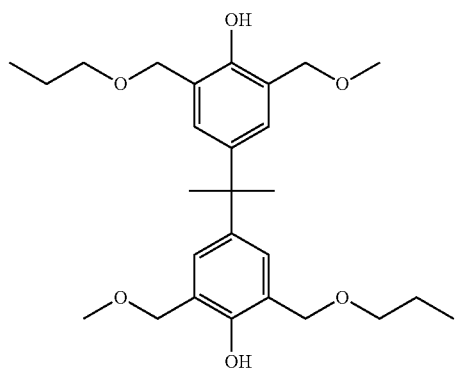
Formula (3-15)
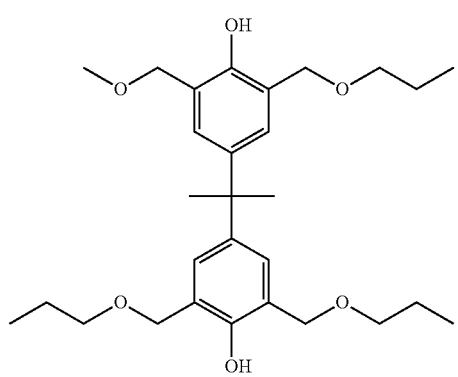
Formula (3-16)
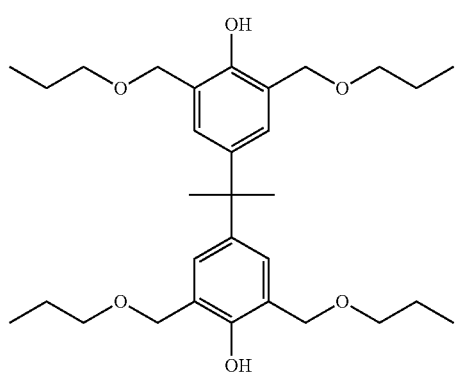
Formula (3-17)
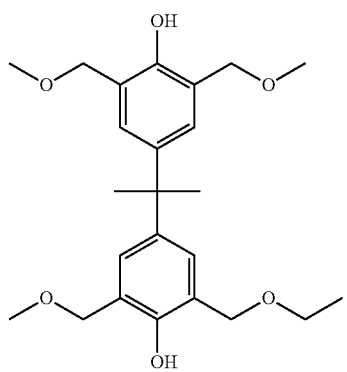

Formula (3-18)
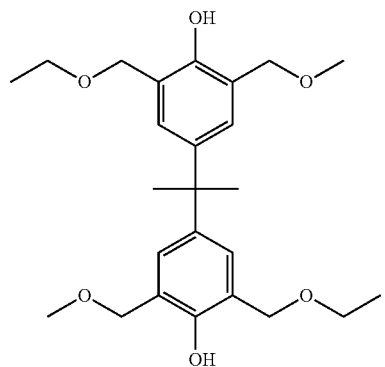
Formula (3-19)
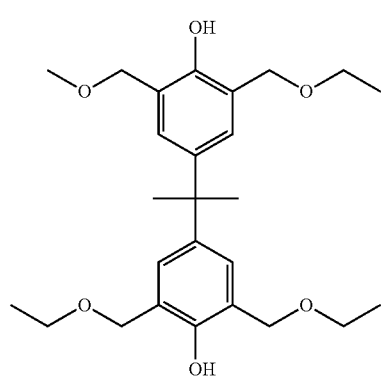
Formula (3-20)
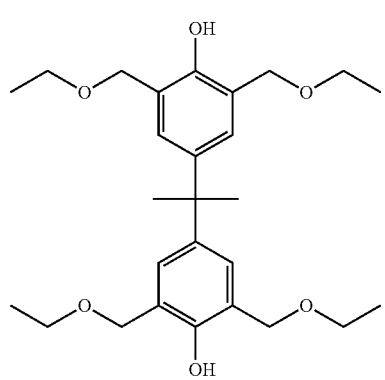
Formula (3-21)
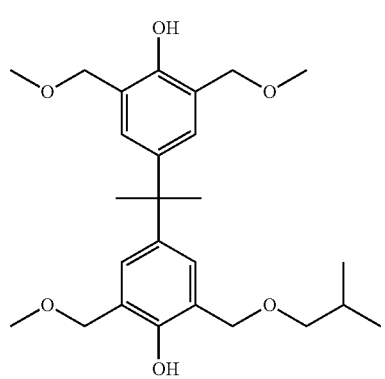
Formula (3-22)
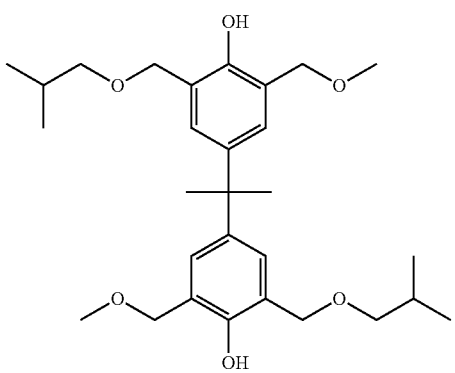
Formula (3-23)
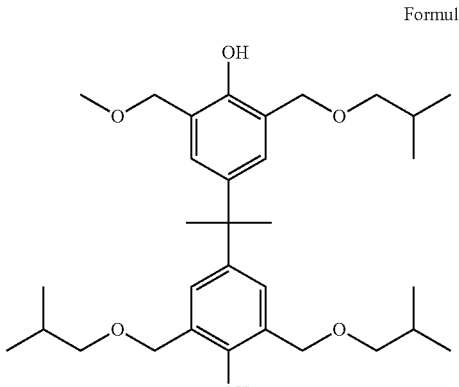
Formula (3-24)
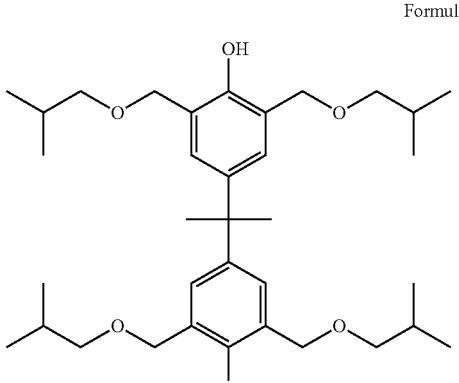
Formula (3-25)
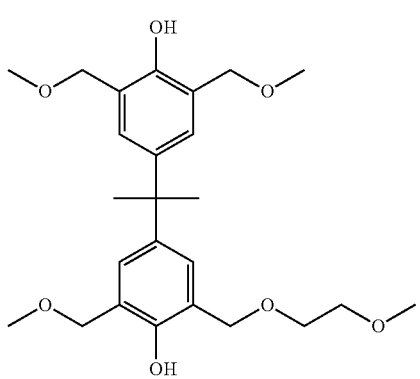

Formula (3-26)
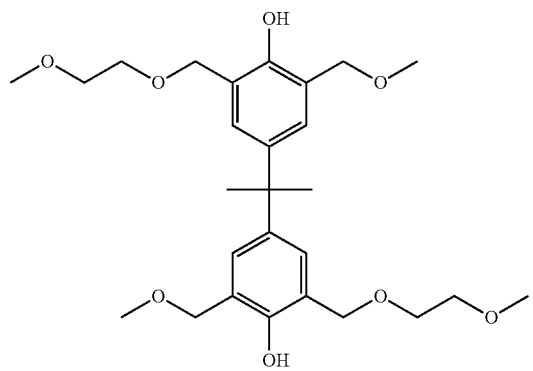
Formula (3-27)
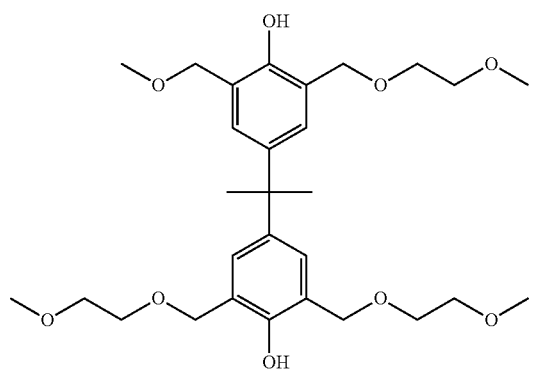
Formula (3-28)
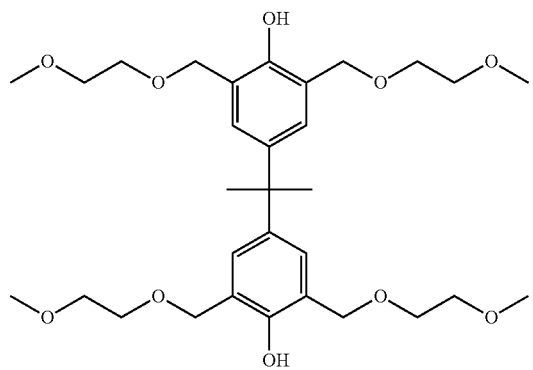
Formula (3-29)
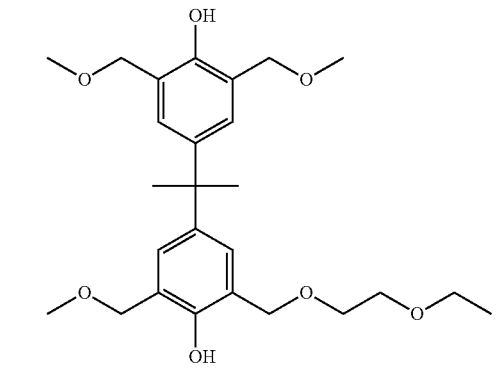
Formula (3-30)
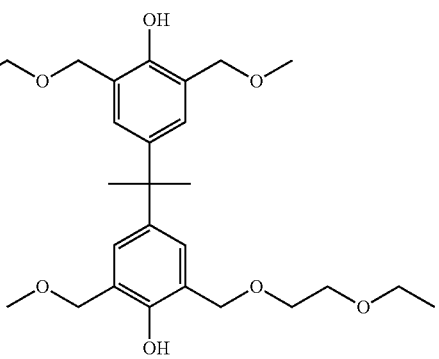
Formula (3-31)
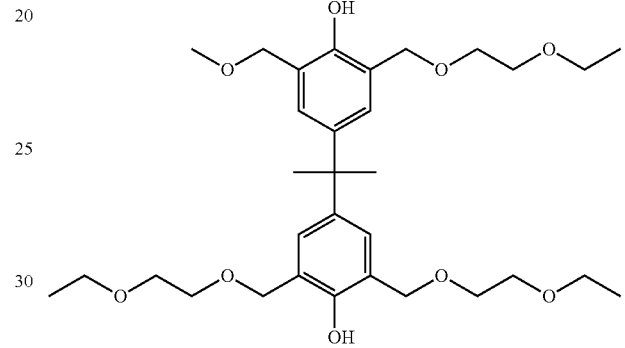
Formula (3-32)
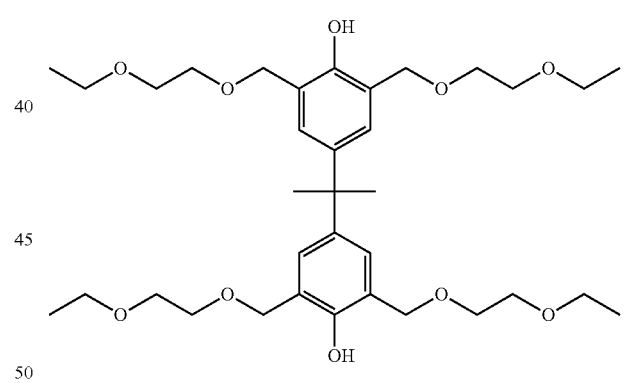
Formula (3-33)
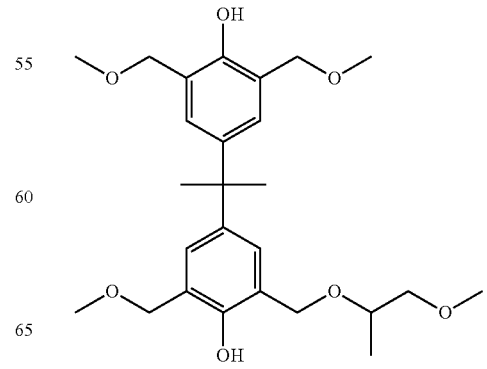

Formula (3-34)
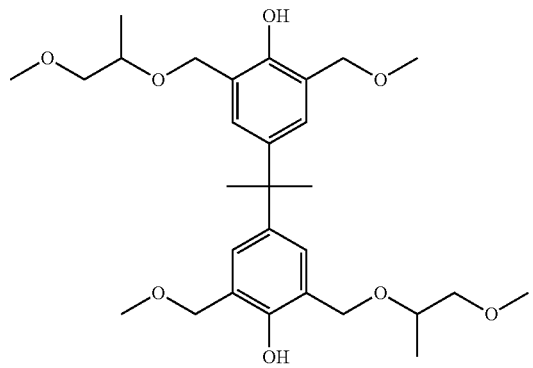
Formula (3-35)
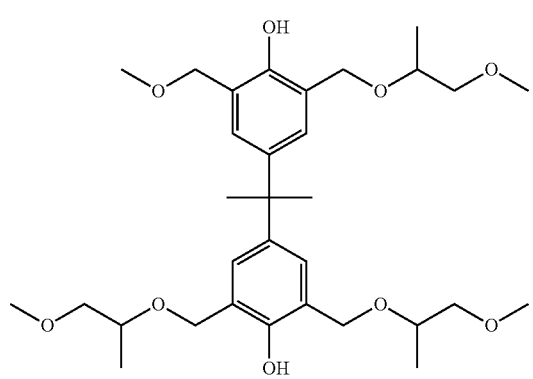
Formula (3-36)
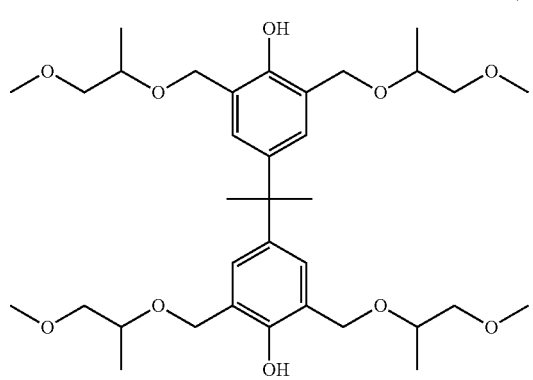
Formula (3-37)
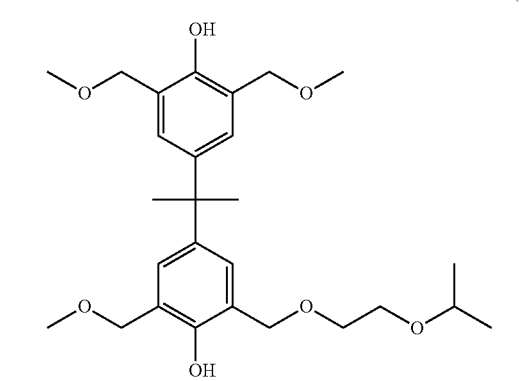
Formula (3-38)
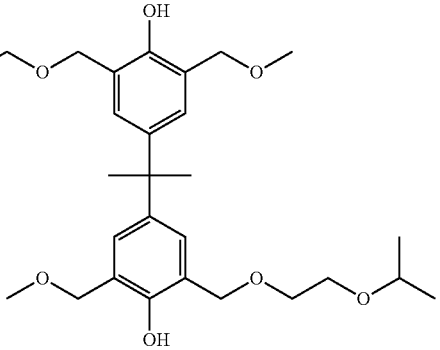
Formula (3-39)
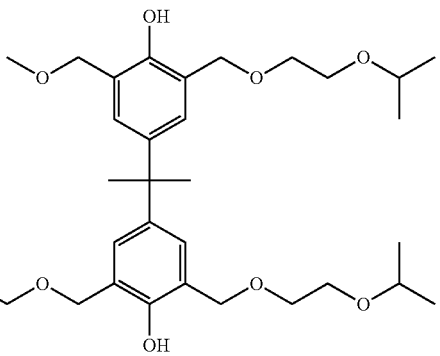
Formula (3-40)
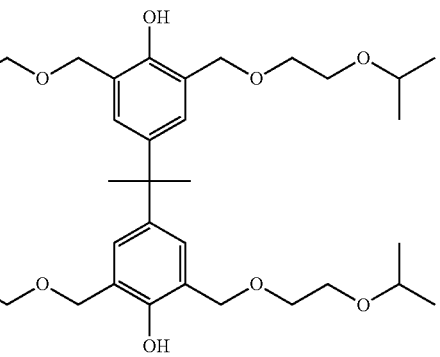
The compound of Formula (3) or Formula (4) used in the present invention, for example, can be exemplified as follows:
Formula (4-1)
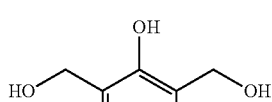
Formula (4-2)
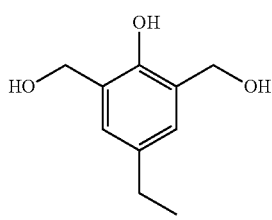

-continued
Formula (4-3)
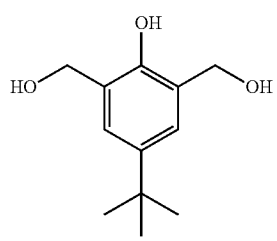
Formula (4-4)
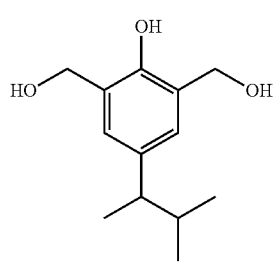
Formula (4-5)
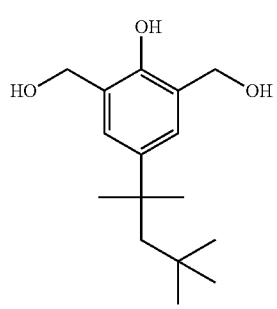
Formula (4-6)
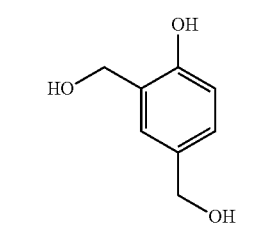
Formula (4-7)
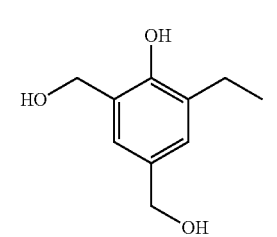
Formula (4-8)
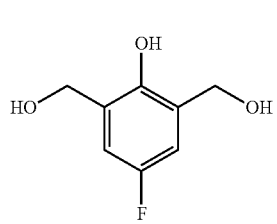
Formula (4-9)
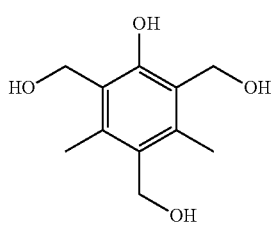
Formula (4-10)
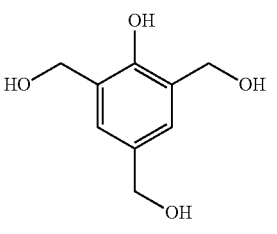
Formula (4-11)
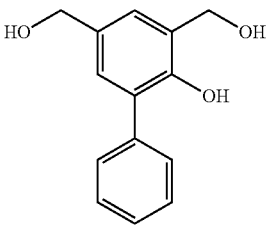
Formula (4-12)
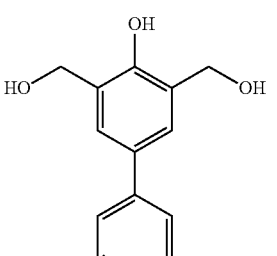
Formula (4-13)
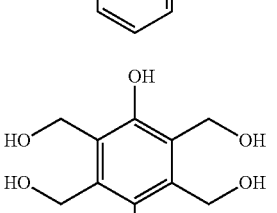
Formula (4-14)
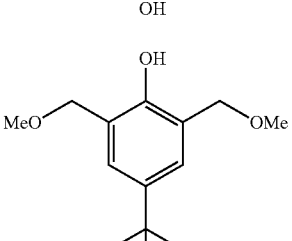
Formula (4-15)
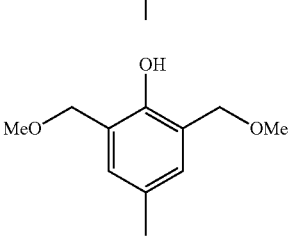

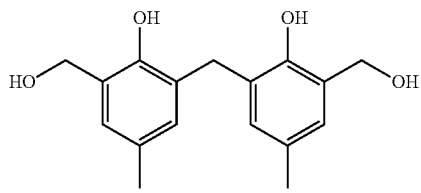
Formula (4-16)

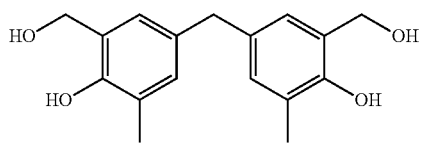
Formula (4-17)

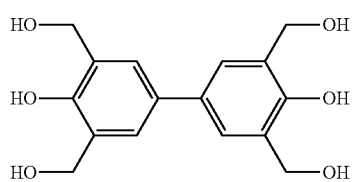
Formula (4-18)

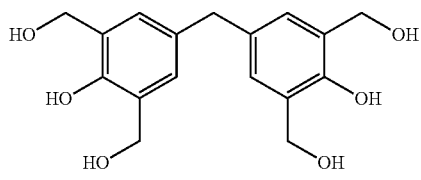
Formula (4-19)

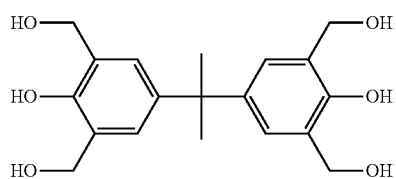
Formula (4-20)

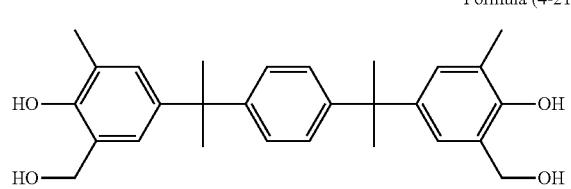
Formula (4-21)

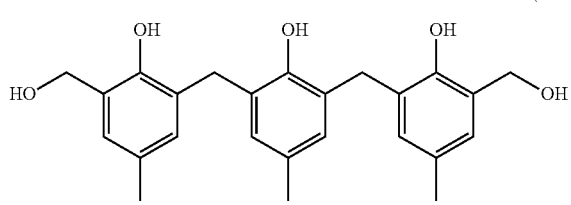
Formula (4-22)

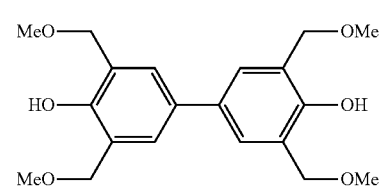
Formula (4-23)

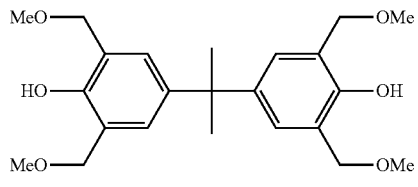
Formula (4-24)

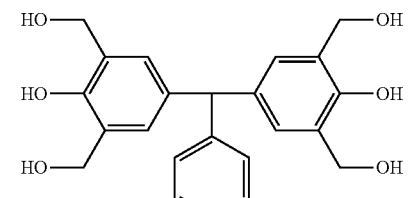
Formula (4-25)

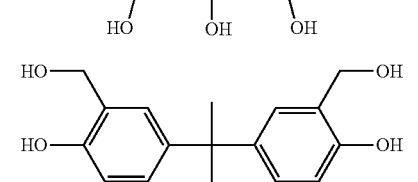
Formula (4-26)

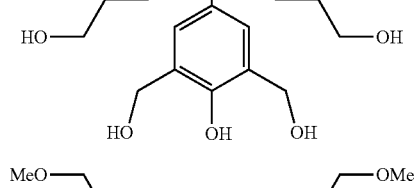
Formula (4-27)

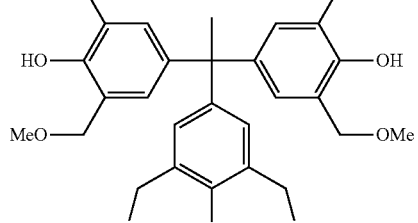

As the resin used in the present invention, a resin can be used as long as this resin can form a crosslinking reaction with the crosslinkable compound. Examples of the crosslink forming group existing in the resin may include a hydroxy group, a carboxy group, an amino group, and an alkoxy group.

Examples of the resin having these crosslink forming groups may include an acrylic resin and a novolac resin, and the novolac resin can be preferably used.

The novolac resin can be obtained by reacting an aromatic ring-containing compound with an aldehyde compound or a ketone compound in the presence of an acid catalyst. Examples of the aromatic ring-containing compound may include benzene, phenol, naphthalene, phloroglucinol, hydroxynaphthalene, fluorene, carbazole, bisphenol, bisphenol S, diphenylamine, triphenylamine, phenylnaphthylamine, anthracene, hydroxyanthracene, phenothiazine, phenoxazine, phenylindole, and polyphenols.

Examples of the aldehyde may include saturated aliphatic aldehydes such as formaldehyde, paraformaldehyde, acetaldehyde, propylaldehyde, butyraldehyde, isobutyraldehyde, valeraldehyde, capronaldehyde, 2-methylbutyraldehyde, hexylaldehyde, undecanealdehyde, 7-methoxy-3,7-dimethyloctylaldehyde, cyclohexanealdehyde, 3-methyl-2-butyraldehyde, glyoxal, malonaldehyde, succinaldehyde, glutaraldehyde, and adipaldehyde, unsaturated aliphatic aldehydes such as acrolein and methacrolein, heterocyclic aldehydes such as furfural and pyridinealdehyde, and aromatic aldehydes such as benzaldehyde, naphthylaldehyde, anthrylaldehydes, phenanthrylaldehydes, salicylaldehyde, phenylacetaldehyde, 3-phenylpropionaldehyde, tolylaldehyde, (N,N-dimethylamino)benzaldehyde, acetoxybenzaldehyde, and 1-pyrenecarboxaldehyde.

Examples of the ketone may include diaryl ketones such as diphenyl ketone, phenyl naphthyl ketone, dinaphthyl ketone, phenyl tolyl ketone, ditolyl ketone, and 9-fluorenone.

The novolac resin used in the present invention is a resin obtained by condensing the aromatic ring-containing compound with the aldehyde compound or the ketone compound. In this condensation reaction, the aldehydes or the ketones can be used in a ratio of 0.1 equivalent to 10 equivalents relative to 1 equivalent of the phenyl group contained in the heterocyclic group-containing aromatic compound and participating in the reaction.

Examples of the acid catalyst used in the condensation reaction may include mineral acids such as sulfuric acid, phosphoric acid, and perchloric acid; organic sulfonic acids such as p-toluenesulfonic acid, and p-toluenesulfonic acid monohydrate; and carboxylic acids such as formic acid and oxalic acid. The amount of the acid catalyst to be used is selected depending on the type of the acid catalyst to be used. The amount is usually 0.001 part by mass to 10,000 parts by mass, preferably 0.01 part by mass to 1,000 parts by mass, and more preferably 0.1 part by mass to 100 parts by mass relative to 100 parts by mass of the compound comprising an aromatic ring.

The condensation reaction may be carried out without solvent. The condensation reaction is, however, usually carried out with solvent. All of the solvents can be used as long as the solvents do not inhibit the reaction. Examples of the solvent may include ring ethers such as tetrahydrofuran and dioxane. When the acid catalyst to be used is a liquid acid such as formic acid, the acid can also act as a solvent. The reaction temperature at the time of condensation is usually 40° C. to 200° C. The reaction time is variously selected depending on the reaction temperature and usually about 30 minutes to about 50 minutes.

In the present invention, as a catalyst for promoting the crosslinking reaction of the resin with the crosslinkable compound of Formula (1) or Formula (2), acidic compounds such as p-toluenesulfonic acid, trifluoromethanesulfonic acid, pyridinium p-toluenesulfonate, salicylic acid, 5-sulfosalicylic acid, 4-phenolsulfonic acid, camphorsulfonic acid, 4-chlorobenzenesulfonic acid, benzenedisulfonic acid, 1-naphthalenesulfonic acid, citric acid, benzoic acid, hydroxybenzoic acid, and naphthalene carboxylic acid and/or thermal acid generators such as 2,4,4,6-tetrabromocyclohexadienone, benzoin tosylate, 2-nitrobenzyl tosylate, and other organic sulfonic acid alkyl esters, onium salt-based photoacid generators such as bis(4-t-butylphenyl)iodonium trifluoromethanesulfonate and triphenylsulfonium trifluoromethanesulfonate, halogen-containing compound-based photoacid generators such as phenyl-bis(trichloromethyl)-s-triazine, or sulfonic acid-based photoacid generators such as benzoin tosylate and N-hydroxysuccinimide trifluoromethanesulfonate can be added in combination. The amount of the crosslinking catalyst is 0.0001% by mass to 20% by mass, preferably 0.0005% by mass to 10% by mass, and more preferably 0.01% by mass to 3% by mass relative to the whole solid content.

To the resist underlayer film-forming composition for lithography of the present invention, for example, a light absorbent, a rheology modifier, an adhesion assistance agent, or a surfactant can be further added in addition to the components described above if necessary.

The resist underlayer film-forming composition for lithography can further contain crosslinking agents other than the crosslinking agent compound of Formula (1) or Formula (2). Examples of the crosslinking agent may include a melamine-based agent, a substituted urea-based agent, or a polymer-based agent thereof. The crosslinking agent preferably has at least two crosslink-forming substituents. Examples of the crosslinking agent may include compounds such as methoxymethylated glycoluril, butoxymethylated glycoluril, methoxymethylated melamine, butoxymethylated melamine, methoxymethylated benzoguanamine, butoxymethylated benzoguanamine, methoxymethylated urea, butoxymethylated urea, methoxymethylated thiourea, or methoxymethylated thiourea. A condensate of these compounds can also be used.

As further light absorbents, for example, commercially available light absorbents described in "Kogyoyo Shikiso no Gijutu to Shijyo (Technology and Market of Industrial Colorant)" (CMC Publishing Co., Ltd) and "Senryo Binran (Dye Handbook)" (The Society of Synthetic Organic Chemistry, Japan) can be preferably used. Preferably useable examples of the commercially available light absorbents include C. I. Disperse Yellow 1, 3, 4, 5, 7, 8, 13, 23, 31, 49, 50, 51, 54, 60, 64, 66, 68, 79, 82, 88, 90, 93, 102, 114, and 124; C. I. Disperse Orange 1, 5, 13, 25, 29, 30, 31, 44, 57, 72, and 73; C. I. Disperse Red 1, 5, 7, 13, 17, 19, 43, 50, 54, 58, 65, 72, 73, 88, 117, 137, 143, 199, and 210; C. I. Disperse Violet 43; C. I. Disperse Blue 96; C. I. Fluorescent Brightening Agent 112, 135, and 163; C. I. Solvent Orange 2 and 45; C. I. Solvent Red 1, 3, 8, 23, 24, 25, 27, and 49; C. I. Pigment Green 10; and C. I. Pigment Brown 2. The light absorbents are usually added in a ratio of 10% by mass or less, and preferably in a ratio of 5% by mass or less relative to the whole solid content of the resist underlayer film-forming composition for lithography.

The rheology modifier is added for the purpose of mainly improving flowability of the resist underlayer film-forming composition, and, particularly in a baking process, improving film thickness uniformity of the resist underlayer film and enhancing filling ability of the resist underlayer film-forming composition into the inside of a hole. Specific examples of the rheology modifier may include phthalic acid derivatives such as dimethyl phthalate, diethyl phthalate, diisobutyl phthalate, dihexyl phthalate, and butylisodecyl phthalate, adipic acid derivatives such as di-normal-butyl adipate, diisobutyl adipate, diisooctyl adipate, and octyldecyl adipate, maleic acid derivatives such as di-normal-butylmaleate, diethyl maleate, and dinonyl maleate, oleic acid derivatives such as methyl oleate, butyl oleate, and tetrahydrofurfuryl oleate, or stearic acid derivatives such as normal-butyl stearate, and glyceryl stearate. These rheology modifiers are usually added in a ratio of less than 30% by mass relative to the whole solid content of the resist underlayer film-forming composition for lithography.

The adhesion assistance agent is mainly added so that adhesion between the substrate or the resist and the resist underlayer film-forming composition is improved and that the resist is not peeled, particularly in development. Specific examples of the adhesion assistance agent may include chlorosilanes such as trimethylchlorosilane, dimethylvinylchlorosilane, methyldiphenylchlorosilane, and chloromethyldimethylchlorosilane, alkoxysilanes such as trimethylmethoxysilane, dimethyldiethoxysilane, methyldimethoxysilane, dimethylvinylethoxysilane, diphenyldimethoxysilane, and phenyltriethoxysilane, silazanes such as hexamethyldisilazane, N,N-bis(trimethylsilyl)urea, dimethyltrimethylsilylamine, and trimethylsilylimidazole, silanes such as vinyltrichlorosilane, γ-chloropropyltrimethoxysilane, γ-aminopropyltriethoxysilane, and γ-glycidoxypropyltrimethoxysilane, heterocyclic compounds such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine, and urea compounds or thiourea compounds such as 1,1-dimethylurea and 1,3-dimethylurea. These adhesion assistance agents are usually added in a ratio less than 5% by mass, and preferably in a ratio of less than 2% by mass relative to the whole solid content of the resist underlayer film-forming composition for lithography.

To the resist underlayer film-forming composition for lithography of the present invention, a surfactant can be added for preventing generation of pinholes and striations and further improving applicability to surface unevenness. Examples of the surfactant may include nonionic surfactant such as polyoxyethylene alkyl ethers including polyoxyethylene lauryl ether, polyoxyethylene stearyl ether, polyoxyethylene cetyl ether, and polyoxyethylene oleyl ether; polyoxyethylene alkylallyl ethers including polyoxyethylene octylphenol ether and polyoxyethylene nonylphenol ether; polyoxyethylene-polyoxypropylene block copolymers; sorbitan fatty acid esters including sorbitan monolaurate, sorbitan monopalmitate, sorbitan monostearate, sorbitan monooleate, sorbitan trioleate, and sorbitan tristearate; and polyoxyethylene sorbitan fatty acid esters including polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303, and EF352 (manufactured by Tochem Products, trade name), MEGAFAC F171, F173, and R-30 (manufactured by Dainippon Ink and Chemicals Inc., trade name), Fluorad FC430 and FC431 (manufactured by Sumitomo 3M Ltd., trade name), Asahi guard AG710, Surflon S-382, SC101, SC102, SC103, SC104, SC105, and SC106 (manufactured by Asahi Glass Co., Ltd., trade name); and Organosiloxane Polymer KP341 (manufactured by Shin-Etsu Chemical Co., Ltd.). The amount of the surfactant to be added is usually 2.0% by mass or less and preferably 1.0% by mass or less relative to the whole solid content of the resist underlayer film-forming composition for lithography of the present invention. These surfactants can be added singly or in combination of two or more of them.

In the resist underlayer film-forming composition of the present invention, usable examples of a solvent dissolving the resin, the crosslinking agent component, the crosslinking catalyst, and the like may include ethylene glycol monomethyl ether, ethylene glycol monoethyl ether, methyl cellosolve acetate, ethyl cellosolve acetate, diethylene glycol monomethyl ether, diethylene glycol monoethyl ether, propylene glycol, propylene glycol monomethyl ether, propylene glycol monomethyl ether acetate, propylene glycol monoethyl ether, propylene glycol monoethyl ether acetate, propylene glycol propyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, and butyl lactate. These organic solvents can be used singly or in combination of two or more of them.

In addition, these solvents can be used by mixing with a high boiling point solvent such as propylene glycol monobutyl ether and propylene glycol monobutyl ether acetate. Among these solvents, propylene glycol monomethyl ether, propylene glycol monomethyl ether acetate, ethyl lactate, butyl lactate, and cyclohexanone are preferable for improving a levering property.

The resist used in the present invention is a photoresist or an electron beam resist.

As the photoresist applied on the resist underlayer film for lithography of the present invention, both negative photoresist and positive photoresist can be used. Examples of the resists include a positive photoresist made of a novolac resin and 1,2-naphthoquinonediazidesulfonate, a chemically amplified photoresist made of a binder having a group that increases an alkali dissolution rate by decomposing with an acid and a photoacid generator, a chemically amplified photoresist made of an alkali-soluble binder, a low molecular weight compound that increases an alkali dissolution rate of the photoresist by decomposing with an acid, and a photoacid generator, a chemically amplified photoresist made of a binder having a group that increases an alkali dissolution rate by decomposing with an acid, a low molecular weight compound that increases an alkali dissolution rate of the photoresist by decomposing with an acid, and a photoacid generator, and a photoresist having Si atoms in the skeleton of the molecule. Specific examples may include APEX-E (trade name, manufactured by Rohm and Haas Inc.)

Examples of the electron beam resist applied onto the resist underlayer film for lithography of the present invention may include a composition made of a resin containing Si—Si bonds in the main chain and containing an aromatic ring at its end and an acid generator generating an acid by irradiation with electron beams and a composition made of poly(p-hydroxystyrene) in which an organic group containing N-carboxyamine is substituted for a hydroxy group and an acid generator generating an acid by irradiation with electron beams. In the latter electron beam resist composition, the acid generated from the acid generator by the electron beam irradiation is reacted with the N-carboxyaminoxy group of the polymer side chain and the polymer side chain is decomposed into a hydroxy group to exhibit alkali solubility. Consequently, the resist composition is dissolved into an alkali development liquid to form a resist pattern. Examples of the acid generator generating the acid by electron beam irradiation may include halogenated organic compounds such as 1,1-bis[p-chlorophenyl]-2,2,2-trichloroethane, 1,1-bis[p-methoxyphenyl]-2,2,2-trichloroethane, 1,1-bis[p-chlorophenyl]-2,2-dichloroethane, and 2-chloro-6-(trichloromethyl)pyridine, onium salts such as triphenylsulfonium salts and diphenyliodonium salts, and sulfonates such as nitrobenzyltosylate and dinitrobenzyltosylate.

As the development liquid for the resist having the resist underlayer film formed by using the resist underlayer film film-forming composition for lithography of the present invention, the following aqueous alkali solutions can be used. The aqueous alkali solutions includes solutions of inorganic alkalis such as sodium hydroxide, potassium hydroxide, sodium carbonate, sodium silicate, sodium metasilicate, and aqueous ammonia; primary amines such as ethylamine and n-propylamine; secondary amines such as diethylamine and di-n-butylamine; tertiary amines such as triethylamine and methyldiethylamine; alcoholamines such as dimethylethanolamine and triethanolamine; quaternary ammonium salt such as tetramethylammonium hydroxide, tetraethylammonium hydroxide, and choline; and cyclic amines such as pyrrole and piperidine. To the aqueous solutions of the alkalis described above, an adequate amount of alcohols such as isopropyl alcohol or a surfactant such as a nonionic surfactant can be added and the mixture can be used. Among these development liquids, aqueous solutions of the quaternary ammonium salts are preferable and aqueous solutions of tetramethylammonium hydroxide and choline are further preferable.

Subsequently, a method for forming the resist pattern of the present invention will be described. The resist underlayer film-forming composition is applied onto a substrate (for example, silicon/silicon dioxide coating, a glass substrate and a transparent substrate such as an ITO substrate) for use in producing precision integrated circuit elements by an appropriate application method such as a spinner and a coater and thereafter the applied composition is cured by baking to form an application type underlayer film. A film thickness of the resist underlayer film is preferably 0.01 μm to 3.0 μm. Conditions for baking after the application are 80° C. to 350° C. for 0.5 minute to 120 minutes. Thereafter, the resist is directly applied onto the resist underlayer film or applied after forming a film made of one layer or several layers of coating material on the application type underlayer film if necessary. Thereafter, the resist is irradiated with light or electron beams through the predetermined mask and is developed, rinsed, and dried to be able to obtain an excellent resist pattern. Post Exposure Bake (PEB) of light or electron beams can also be carried out if necessary. The part of the resist underlayer film where the resist is removed by the previous process is removed by dry etching to be able to form a desired pattern on the substrate.

The exposure light of the photoresist is actinic rays such as near ultraviolet rays, far ultraviolet rays, or extreme ultraviolet rays (for example, EUV, wavelength 13.5 nm) and, for example, light having a wavelength of 248 nm (KrF laser light), 193 nm (ArF laser light), or 157 nm ($F_2$ laser light) is used. Any light irradiation method can be used without limitation as long as the acid is generated from the photoacid generator. An exposure amount is 1 mJ/cm$^2$ to 2,000 mJ/cm$^2$, or 10 mJ/cm$^2$ to 1,500 mJ/cm$^2$, or 50 mJ/cm$^2$ to 1,000 mJ/cm$^2$.

The electron beam irradiation to the electron beam resist can be carried out by, for example, using an electron beam irradiation device.

In the present invention, a semiconductor device can be produced through steps of forming a resist underlayer film by using the resist underlayer film-forming composition of the present invention onto a semiconductor substrate; forming a resist film on the underlayer film; forming a resist pattern by irradiation with light or electron beams and development; etching the resist underlayer film by using the formed resist pattern; and processing the semiconductor substrate by using the patterned resist underlayer film.

When the formation of the finer resist pattern will be progressed in the future, the problem of resolution and the problem of resist pattern collapse after development will occur and thus formation of a thinner resist film will be desired. Consequently, the resist pattern thickness sufficient for substrate processing is difficult to secure. As a result, not only the resist pattern but also the resist underlayer film formed between the resist and the semiconductor substrate to be processed has been required to have the function as a mask at the time of the substrate processing. As the resist underlayer film for such a process, a resist underlayer film for lithography having the selectivity of dry etching rate close to that of the resist, a resist underlayer film for lithography having the selectivity of dry etching rate smaller than that of the resist, or a resist underlayer film for lithography having the selectivity of dry etching rate smaller than that of the semiconductor substrate, which is different from conventional resist underlayer films having high etch rate properties, has been required. Such a resist underlayer film can be provided with the function of anti-reflective properties and thus can also have the function of an anti-reflective coating.

On the other hand, in order to obtain a finer resist pattern, a process has been also started to be used in which the resist pattern and the resist underlayer film at the time of resist underlayer film dry etching are formed more narrowly than the pattern width at the time of resist development. As the resist underlayer film for such a process, the resist underlayer film having the selectivity of dry etching rate close to that of the resist, which is different from conventional high etching rate anti-reflective coatings, has been required. Such a resist underlayer film can be provided with the anti-reflective properties and thus can also have the function of the conventional anti-reflective coating.

In the present invention, after the resist underlayer film of the present invention is formed onto the substrate, the resist can be applied directly onto the resist underlayer film or after a film made of a single layer or several layers of coating material is formed onto the resist underlayer film. This enables the pattern width of the resist to be narrow. Even when the resist is thinly covered in order to prevent pattern collapse, the substrate can be processed by selecting an appropriate etching gas.

More specifically, the semiconductor device can be manufactured through steps of: forming a resist underlayer film onto a semiconductor substrate using the resist underlayer film-forming composition; forming a hard mask on the resist underlayer film using a coating material containing a silicon component and the like or a hard mask (for example, silicon nitride oxide) by vapor deposition; forming a resist film on the hard mask; forming a resist pattern by irradiation with light or an electron beam and development; etching the hard mask using the formed resist pattern with a halogen-based gas; etching the resist underlayer film using the patterned hard mask with an oxygen-based gas or a hydrogen-based gas; and processing the semiconductor substrate using the patterned resist underlayer film with the halogen-based gas.

In consideration of the effect as the anti-reflective coating, the resist underlayer film-forming composition for lithography of the present invention includes a light absorption site in the skeleton and thus no substances are diffused into the photoresist at the time of drying by heating. The light absorption site has sufficiently large light absorption properties and thus has a high anti-reflection effect.

The resist underlayer film-forming composition for lithography of the present invention has high heat stability, prevents contamination to the upper layer film caused by decomposed substances generated at the time of baking, and can provide an extra temperature margin during the baking process.

Depending on process conditions, the resist underlayer film-forming composition for lithography of the present invention can be used as a film that has the anti-reflection function and further has a function that prevents interaction between the substrate and the photoresist or prevents adverse effect on the substrate due to the materials for use in the photoresist or substances generated at the time of light exposure to the photoresist.

The present invention also relates to a new compound of Formula (5):

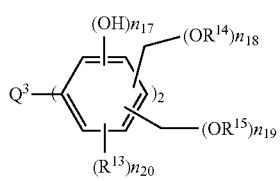

Formula (5)

(where $Q^3$ is an isopropylidene group (—C(CH$_3$)$_2$—); $R^{14}$ is a $C_{2-10}$ alkyl group or a $C_{2-10}$ alkyl group having a $C_{1-10}$ alkoxy group; $R^{15}$ is a hydrogen atom or a methyl group; $R^{13}$ is a $C_{1-10}$ alkyl group or a $C_{6-40}$ aryl group;

n17 is an integer of 1≤n17≤3; n18 is an integer of 1≤n18≤4; n19 is an integer of 0≤n19≤3; n20 is an integer of 0≤n20≤3; and a total of the integers is an integer of 2≤(n17+n18+n19+n20)≤5).

As the alkyl group, the alkoxy group, and the aryl group, the above examples can be exemplified.

EXAMPLES

Synthesis Example 1

To a 100 mL recovery flask, TMOM-BP (20.00 g, 0.055 mol, manufactured by Honshu Chemical Industry Co., Ltd., Formula (4-23)) and PGME (propylene glycol monomethyl ether, 80.00 g) were charged and the mixture was stirred. The temperature of the mixture was raised until reflux was confirmed to dissolve the mixture and to start polymerization. 24 hours later, the reaction product was left to cool down to 30° C. Thereafter, TMOM-BP-PGME (a compound corresponding to Formula (3-4) was a main product and compounds of Formula (3-1), Formula (3-2), and Formula (3-3) were mixed in the compound of Formula (3-4)) in the PGME solution was obtained. As a result of identification of an existence ratio of the tetra-substituted compound of TMOM-BP-PGME carried out by GPC, the tetra-substituted compound existed in a ratio of 34 mol % in the whole TMOM-BP-PGME.

Synthesis Example 2

To a 200 mL recovery flask, TMOM-BP (5.00 g, 0.014 mol, manufactured by Honshu Chemical Industry Co., Ltd., Formula (4-23)), washed 15JWET (20.00 g, trade name Amberlist, manufactured by The Dow Chemical Company) as an ion-exchange resin catalyst, and PGME (propylene glycol monomethyl ether, 75.00 g) were charged and the mixture was stirred. The temperature of the mixture was raised until reflux was confirmed to dissolve the mixture and to start polymerization. 48 hours later, the reaction product was left to cool down to 60° C. Thereafter, 15JWET was removed by filtration and the obtained precipitate was filtered to give a target product (a compound corresponding to Formula (3-4) was a main product and compounds of Formula (3-1), Formula (3-2), and Formula (3-3) were mixed in the compound of Formula (3-4), hereinafter abbreviated as TMOM-BP-PGME2).

As a result of identification of an existence ratio of the tetra-substituted compound of TMOM-BP-PGME2 carried out by GPC, the tetra-substituted compound existed in a ratio of 68 mol % in the whole TMOM-BP-PGME2.

Synthesis Example 3

To a 200 mL four-necked flask, TMOM-BP (3.00 g, 0.008 mol, manufactured by Honshu Chemical Industry Co., Ltd., Formula (4-23)) and washed 15JWET (12.00 g, trade name Amberlist, manufactured by The Dow Chemical Company) as an ion-exchange resin catalyst were added and butanol (60.00 g, manufactured by KANTO CHEMICAL CO., INC.) was charged. The mixture was stirred to start polymerization at 100° C. 48 hour later, the reaction product was left to cool down to 30° C. Thereafter, 15JWET was removed by filtration and the filtrate was concentrated at 30° C. under reduced pressure for 2 hours and dried to give 2.9 g of the target material (hereinafter abbreviated as TBOM-BP-BU; a compound corresponding to Formula (3-8) was a main product and compounds of Formula (3-5), Formula (3-6), and Formula (3-7) were mixed in the compound of Formula (3-8)).

Structure analysis was carried out with $^1$H-NMR to confirm that the target compound was obtained. The existence ratio of the tetra-substituted compound of TBOM-BP-BU was confirmed to be 85 mol % in the whole TBOM-BP-BU with HPLC.

The NMR spectrum of the tetra-substituted compound of TBOM-BP-BU showed the following characteristic absorptions (FIG. 1).

$^1$H-NMR (500 MHz, DMSO-d6): 0.89 ppm (t, 12H), 1.36 ppm (m, 8H), 1.54 ppm (m, 8H), 3.49 (t, 8H), 4.54 (s, 8H), 7.34 (s, 4H), 8.50 (s, 2H).

Synthesis Example 4

To a 200 mL four-necked flask, TM-BIP-A (3.00 g, 0.009 mol, manufactured by Honshu Chemical Industry Co., Ltd., Formula (4-24)) and washed 15JWET (12.00 g, trade name Amberlist, manufactured by The Dow Chemical Company) as an ion-exchange resin catalyst were added and butanol (60.00 g, manufactured by KANTO CHEMICAL CO., INC.) was charged. The mixture was stirred to start polymerization at 100° C. 3.5 hours later, the reaction product was left to cool down to 30° C. Thereafter, 15JWET was removed by filtration and the filtrate was concentrated at 30° C. under reduced pressure for 2 hours and dried to give 3.0 g of the target material (a compound corresponding to Formula (3-12) was a main product and compounds of Formula (3-9), Formula (3-10), and Formula (3-11) were mixed in the compound of Formula (3-12); hereinafter abbreviated as TBOM-BIP-A).

Structure analysis was carried out with $^1$H-NMR to confirm that the target compound was obtained. The existence ratio of the tetra-substituted compound of TBOM-BIP-A was confirmed to be 95 mol % in the whole TBOM-BIP-A with HPLC.

Figure 2:
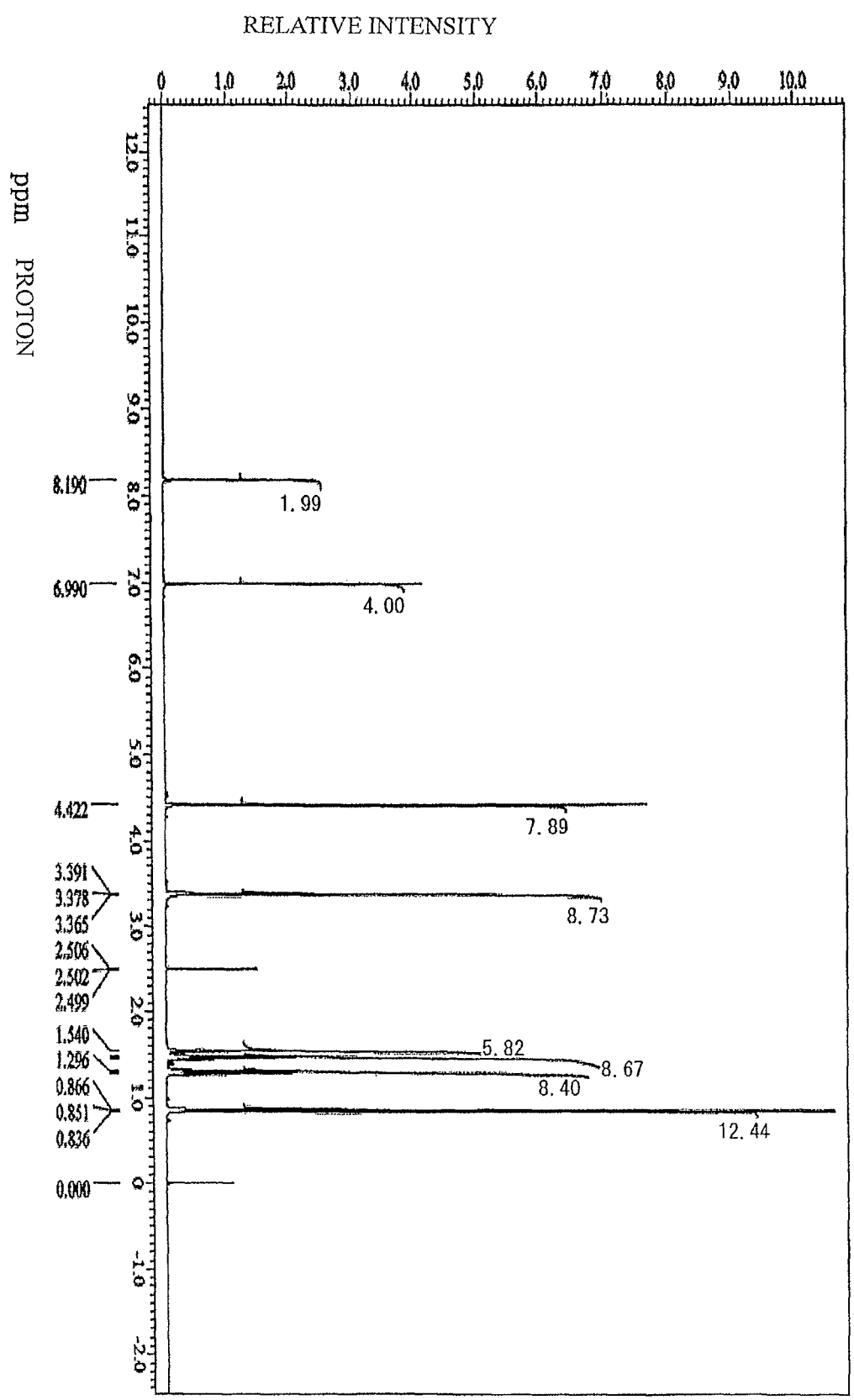
FIG. 2 is an NMR spectrum of the tetra-substituted compound of TBOM-BIP-A obtained in Synthesis Example 4.

The NMR spectrum of the tetra-substituted compound of TBOM-BIP-A showed the following characteristic absorptions (FIG. 2).

$^1$H-NMR (500 MHz, DMSO-d6): 0.85 ppm (t, 12H), 1.30 ppm (m, 8H), 1.47 ppm (m, 8H), 1.54 ppm (s, 6H), 3.38 (t, 8H), 4.42 (s, 8H), 6.99 (s, 4H), 8.19 (s, 2H).

Synthesis Example 5

To a 200 mL four-necked flask, TM-BIP-A (4.00 g, 0.011 mol, manufactured by Honshu Chemical Industry Co., Ltd., Formula (4-24)) and washed 15JWET (16.00 g, trade name Amberlist, manufactured by The Dow Chemical Company) as an ion-exchange resin catalyst were added and 1-propanol (80.00 g, manufactured by KANTO CHEMICAL CO., INC.) was charged. The mixture was stirred to start polymerization at a reflux temperature. 4 hours later, the reaction product was left to cool down to 30° C. Thereafter, 15JWET was removed by filtration and the filtrate was concentrated at 30° C. under reduced pressure for 2 hours and dried to give 5.0 g of the target material (a compound corresponding to Formula (3-16) was a main product and compounds of Formula (3-13), Formula (3-14), and Formula (3-15) were mixed in the compound of Formula (3-16); hereinafter abbreviated as TPOM-BIP-A).

Structure analysis was carried out with $^1$H-NMR to confirm that the target compound was obtained. The existence ratio of the tetra-substituted compound of TPOM-BIP-A was confirmed to be 94 mol % in the whole TPOM-BIP-A with HPLC.

Figure 3:
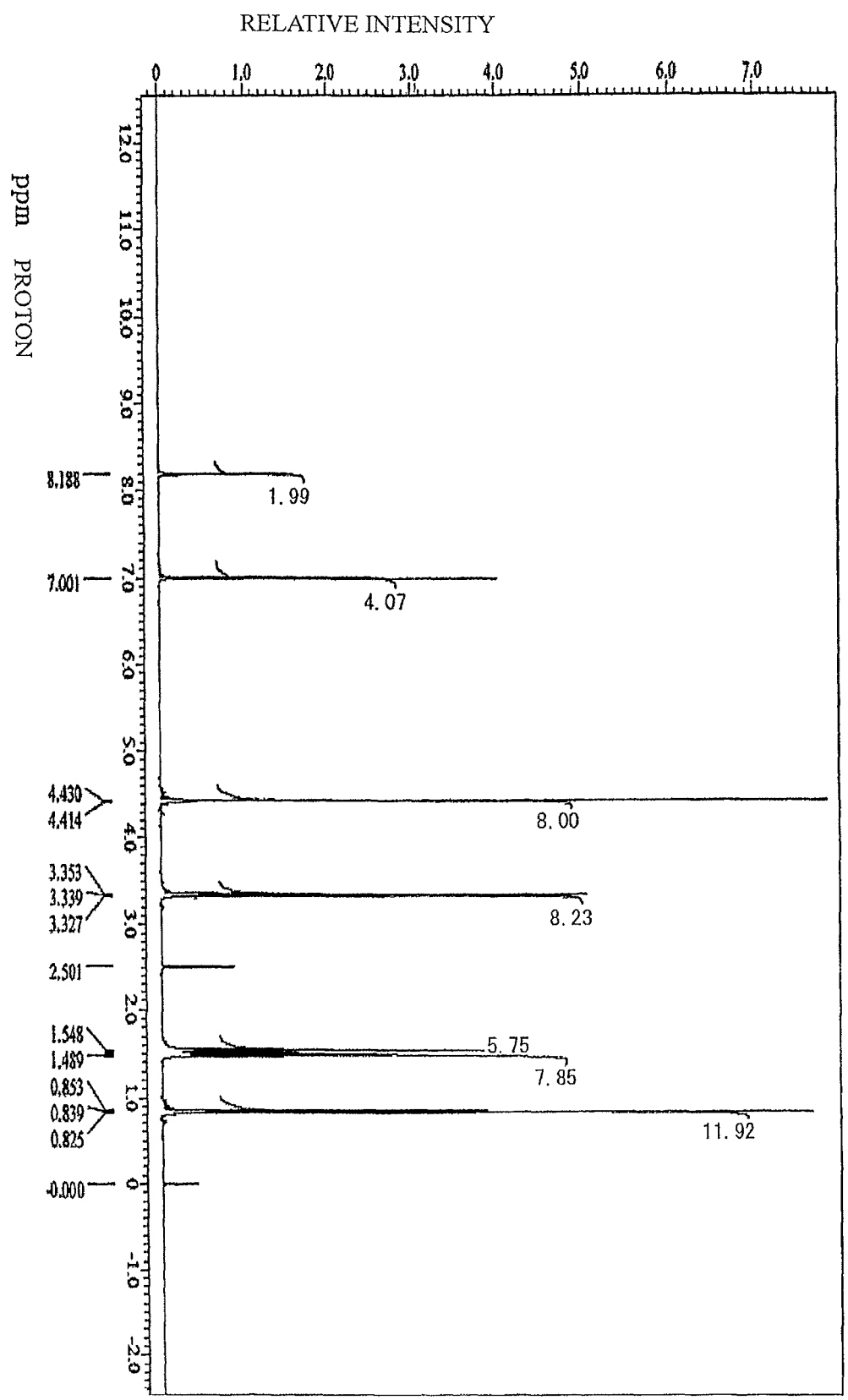
FIG. 3 is an NMR spectrum of the tetra-substituted compound of TPOM-BIP-A obtained in Synthesis Example 5.

The NMR spectrum of the tetra-substituted compound of TPOM-BIP-A showed the following characteristic absorptions (FIG. 3).

$^1$H-NMR (500 MHz, DMSO-d6): 0.84 ppm (t, 12H), 1.49 ppm (m, 8H), 1.55 ppm (s, 6H), 3.34 (t, 8H), 4.43 (s, 8H), 7.00 (s, 4H), 8.19 (s, 2H).

Synthesis Example 6

To a 200 mL four-necked flask, TM-BIP-A (4.00 g, 0.011 mol, manufactured by Honshu Chemical Industry Co., Ltd., Formula (4-24)) and washed 15JWET (16.00 g, trade name Amberlist, manufactured by The Dow Chemical Company) as an ion-exchange resin catalyst were added and ethanol (80.00 g, manufactured by KANTO CHEMICAL CO., INC.) was charged. The mixture was stirred to start polymerization at a reflux temperature. 19.5 hours later, the reaction product was left to cool down to 30° C. Thereafter, 15JWET was removed by filtration and the filtrate was concentrated at 30° C. under reduced pressure for 2 hours and dried to give 4.2 g of the target material (a compound corresponding to Formula (3-20) was a main product and compounds of Formula (3-17), Formula (3-18), and Formula (3-19) were mixed in the compound of Formula (3-20); hereinafter abbreviated as TEOM-BIP-A).

Structure analysis was carried out with $^1$H-NMR to confirm that the target compound was obtained. The existence ratio of the tetra-substituted compound of TEOM-BIP-A was confirmed to be 95 mol % in the whole TEOM-BIP-A with HPLC.

Figure 4:
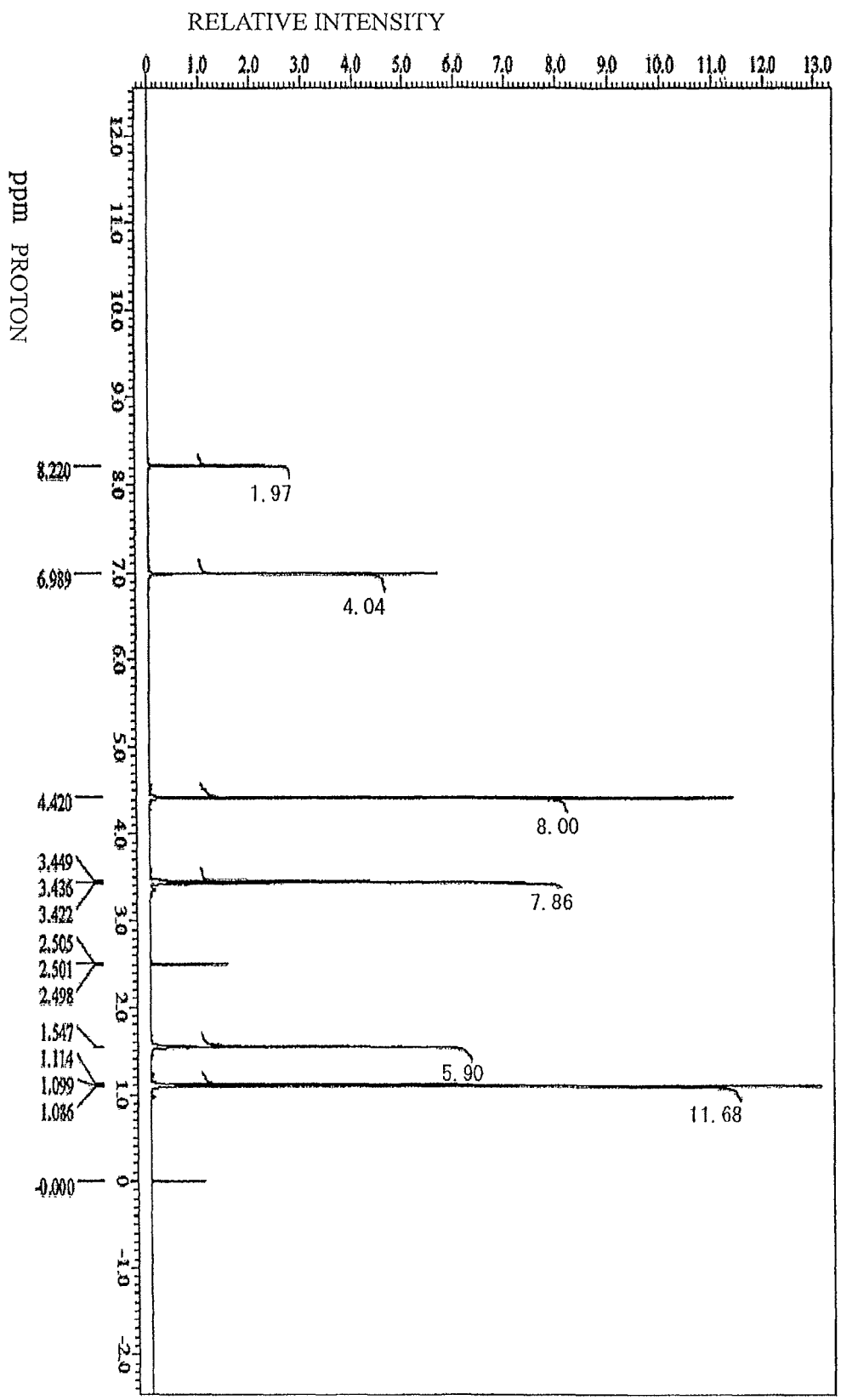
FIG. 4 is an NMR spectrum of the tetra-substituted compound of TEOM-BIP-A obtained in Synthesis Example 6.

The NMR spectrum of the tetra-substituted compound of TEOM-BIP-A showed the following characteristic absorptions (FIG. 4).

$^1$H-NMR (500 MHz, DMSO-d6): 1.10 ppm (t, 12H), 1.55 ppm (s, 6H), 3.44 (q, 8H), 4.42 (s, 8H), 6.99 (s, 4H), 8.22 (s, 2H).

Synthesis Example 7

To a 200 mL four-necked flask, TM-BIP-A (4.00 g, 0.011 mol, manufactured by Honshu Chemical Industry Co., Ltd., Formula (4-24)) and washed 15JWET (16.00 g, trade name Amberlist, manufactured by The Dow Chemical Company) as an ion-exchange resin catalyst were added and 2-methyl-1-propanol (80.00 g, manufactured by KANTO CHEMICAL CO., INC.) was charged. The mixture was stirred to start polymerization at 100° C. 4 hours later, the reaction product was left to cool down to 30° C. Thereafter, 15JWET was removed by filtration and the filtrate was concentrated at 30° C. under reduced pressure for 2 hours and dried to give 5.8 g of the target material (a compound corresponding to Formula (3-24) was a main product and compounds of Formula (3-21), Formula (3-22), and Formula (3-23) were mixed in the compound of Formula (3-24); hereinafter abbreviated as TIBOM-BIP-A).

Structure analysis was carried out with $^1$H-NMR to confirm that the target compound was obtained. The existence ratio of the tetra-substituted compound of TIBOM-BIP-A was confirmed to be 95 mol % in the whole TIBOM-BIP-A with HPLC.

Figure 5:
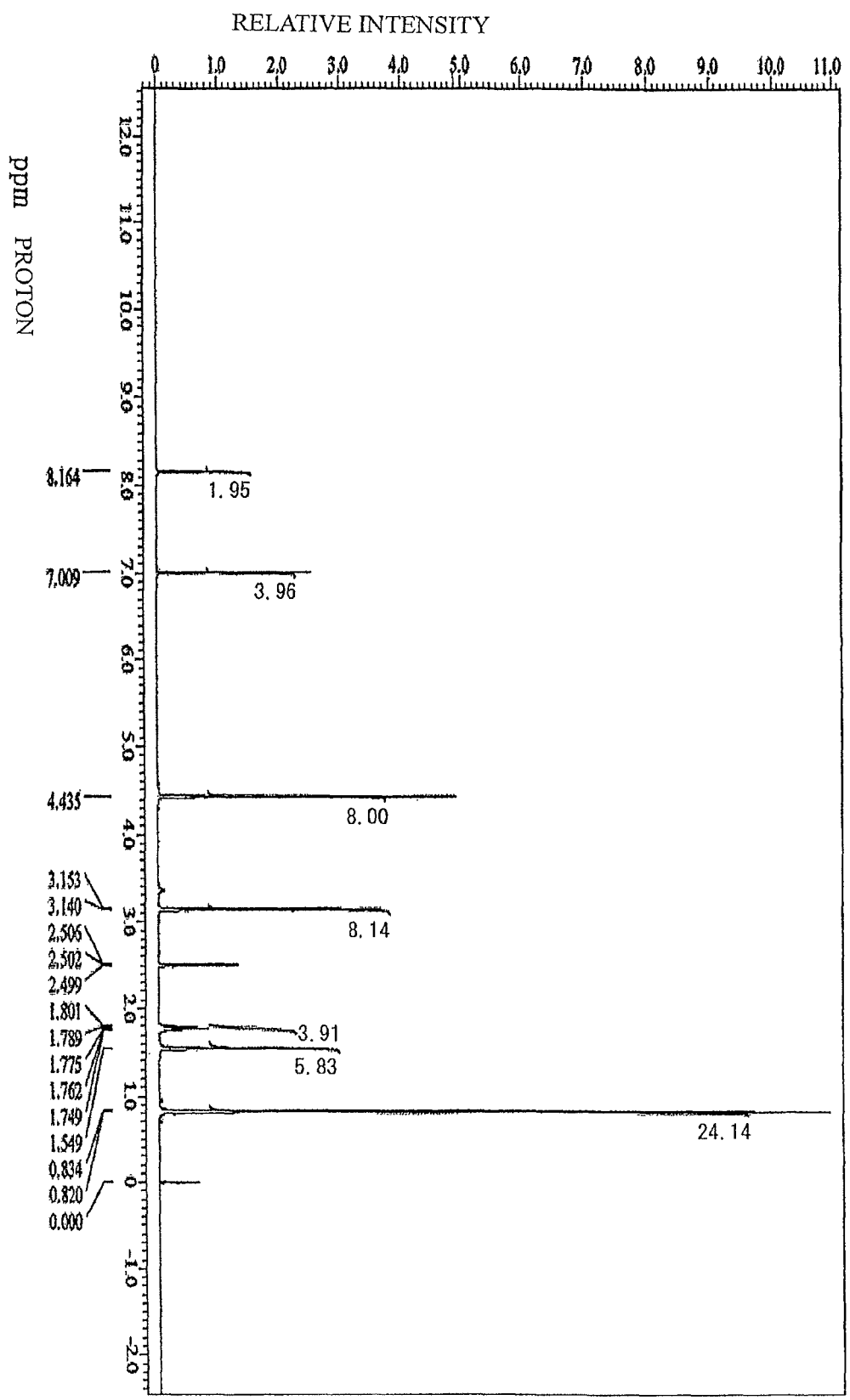
FIG. 5 is an NMR spectrum of the tetra-substituted compound of TIBOM-BIP-A obtained in Synthesis Example 7.

The NMR spectrum of the tetra-substituted compound of TIBOM-BIP-A showed the following characteristic absorptions (FIG. 5).

$^1$H-NMR (500 MHz, DMSO-d6): 0.83 ppm (d, 24H), 1.55 ppm (s, 6H), 1.77 (m, 4H), 3.15 (t, 8H), 4.44 (s, 8H), 7.01 (s, 4H), 8.16 (s, 2H).

Synthesis Example 8

To a 200 mL four-necked flask, TM-BIP-A (4.00 g, 0.011 mol, manufactured by Honshu Chemical Industry Co., Ltd., Formula (4-24)) and washed 15JWET (16.00 g, trade name Amberlist, manufactured by The Dow Chemical Company) as an ion-exchange resin catalyst were added and 2-methoxyethanol (80.00 g, manufactured by KANTO CHEMICAL CO., INC.) was charged. The mixture was stirred to start polymerization at 100° C. One hour later, the reaction product was left to cool down to 30° C. Thereafter, 15JWET was removed by filtration and the filtrate was concentrated at 30° C. under reduced pressure for 2 hours and dried to give 5.3 g of the target material (a compound corresponding to Formula (3-28) was a main product and compounds of Formula (3-25), Formula (3-26), and Formula (3-27) were mixed in the compound of Formula (3-28); hereinafter abbreviated as EGME-BIP-A).

Structure analysis was carried out with $^1$H-NMR to confirm that the target compound was obtained. The existence ratio of the tetra-substituted compound of EGME-BIP-A was confirmed to be 94 mol % in the whole EGME-BIP-A with HPLC.

Figure 6:
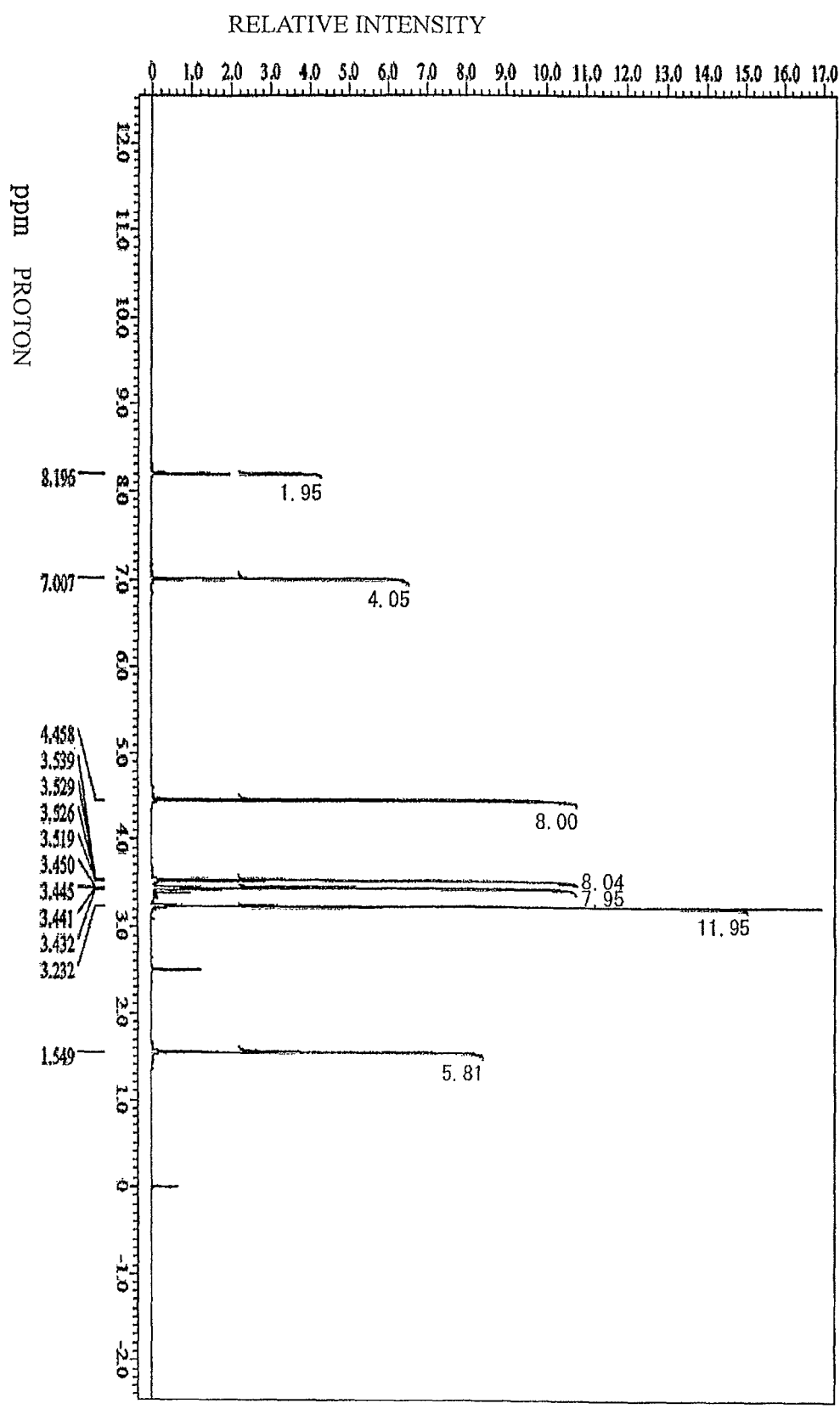
FIG. 6 is an NMR spectrum of the tetra-substituted compound of EGME-BIP-A obtained in Synthesis Example 8.

The NMR spectrum of the tetra-substituted compound of EGME-BIP-A showed the following characteristic absorptions (FIG. 6).

$^1$H-NMR (500 MHz, DMSO-d6): 1.55 ppm (s, 6H), 3.23 ppm (s, 12H), 3.44 ppm (m, 8H), 3.53 ppm (m, 8H), 4.46 (s, 8H), 7.01 (s, 4H), 8.20 (s, 2H).

Synthesis Example 9

To a 200 mL four-necked flask, TM-BIP-A (4.00 g, 0.011 mol, manufactured by Honshu Chemical Industry Co., Ltd., Formula (4-24)) and washed 15JWET (16.00 g, trade name Amberlist, manufactured by The Dow Chemical Company) as an ion-exchange resin catalyst were added and 2-ethoxyethanol (80.00 g, manufactured by KANTO CHEMICAL CO., INC.) was charged. The mixture was stirred to start polymerization at 100° C. One hour later, the reaction product was left to cool down to 30° C. Thereafter, 15JWET was removed by filtration and the filtrate was concentrated at 30° C. under reduced pressure for 2 hours and dried to give 3.0 g of the target material (a compound corresponding to Formula (3-32) was a main product and compounds of Formula (3-29), Formula (3-30), and Formula (3-31) were mixed in the compound of Formula (3-32); hereinafter abbreviated as EGEE-BIP-A).

Structure analysis was carried out with $^1$H-NMR to confirm that the target compound was obtained. The existence ratio of the tetra-substituted compound of EGEE-BIP-A was confirmed to be 92 mol % in the whole EGEE-BIP-A with HPLC.

Figure 7:
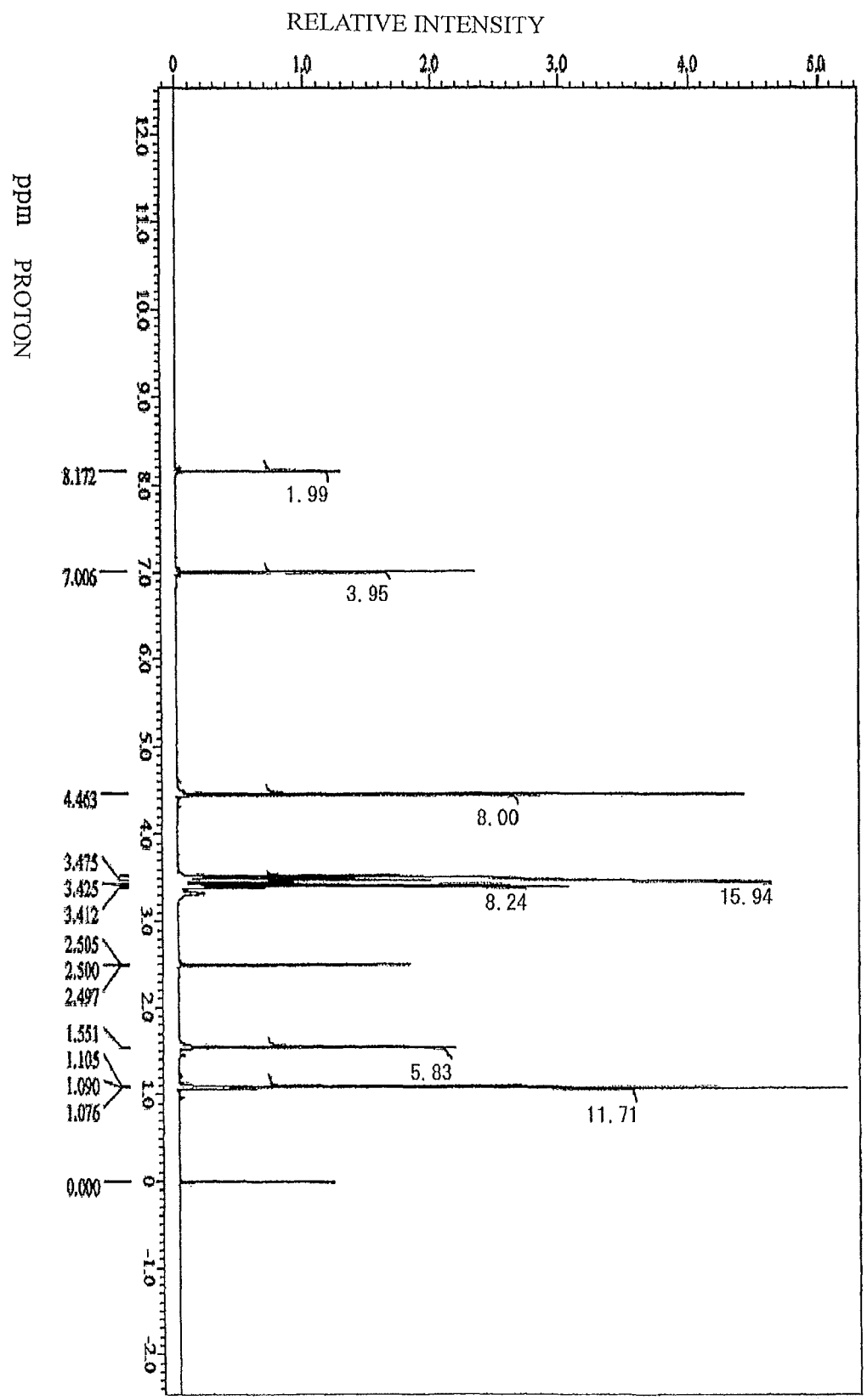
FIG. 7 is an NMR spectrum of the tetra-substituted compound of EGEE-BIP-A obtained in Synthesis Example 9.

The NMR spectrum of the tetra-substituted compound of EGEE-BIP-A showed the following characteristic absorptions (FIG. 7).

$^1$H-NMR (500 MHz, DMSO-d6): 1.09 ppm (t, 12H), 1.55 ppm (s, 6H), 3.42 ppm (m, 8H), 3.5 ppm (m, 16H), 4.46 (s, 8H), 7.01 (s, 4H), 8.17 (s, 2H).

Synthesis Example 10

To a 200 mL four-necked flask, TM-BIP-A (4.00 g, 0.011 mol, manufactured by Honshu Chemical Industry Co., Ltd., Formula (4-24)) and washed 15JWET (16.00 g, trade name Amberlist, manufactured by The Dow Chemical Company) as an ion-exchange resin catalyst were added and PGME (80.00 g, manufactured by KANTO CHEMICAL CO., INC.) was charged. The mixture was stirred to start polymerization at 100° C. One hour later, the reaction product was left to cool down to 30° C. Thereafter, 15JWET was removed by filtration and the filtrate was concentrated at 30° C. under reduced pressure for 2 hours and dried to give 3.0 g of the target material (a compound corresponding to Formula (3-36) was a main product and compounds of Formula (3-33), Formula (3-34), and Formula (3-35) were mixed in the compound of Formula (3-36); hereinafter abbreviated as PGME-BIP-A).

Structure analysis was carried out with $^1$H-NMR to confirm that the target compound was obtained. The existence ratio of the tetra-substituted compound of PGME-BIP-A was confirmed to be 74 mol % in the whole PGME-BIP-A with HPLC.

Figure 8:
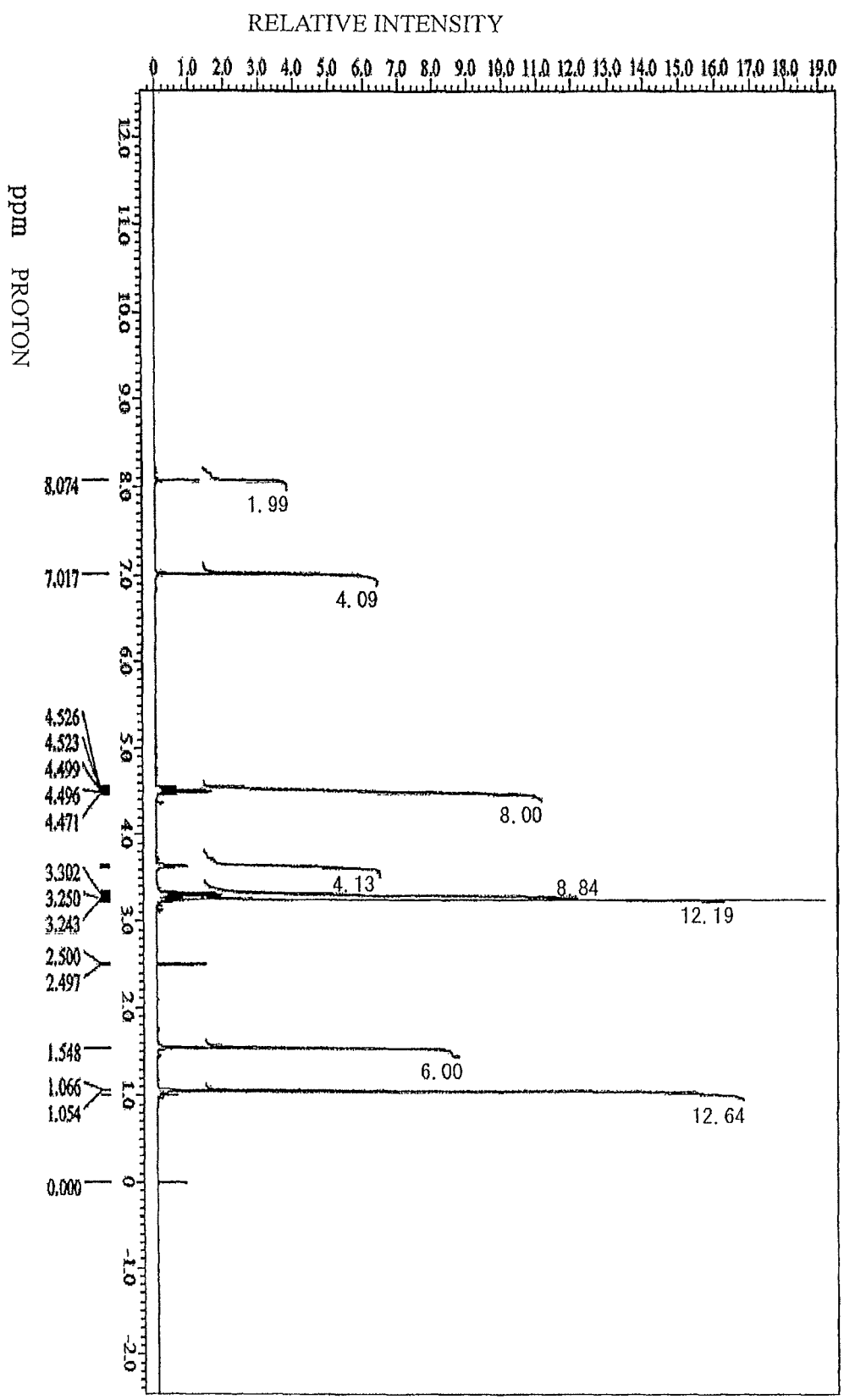
FIG. 8 is an NMR spectrum of the tetra-substituted compound of PGME-BIP-A obtained in Synthesis Example 10.

The NMR spectrum of the tetra-substituted compound of PGME-BIP-A showed the following characteristic absorptions (FIG. 8).

$^1$H-NMR (500 MHz, DMSO-d6): 1.06 ppm (d, 12H), 1.55 ppm, (s, 6H), 3.25 ppm (s, 12H), 3.30 ppm (m, 8H), 3.63 ppm (m, 4H), 4.51 (q, 8H), 7.02 (s, 4H), 8.07 (s, 2H).

Synthesis Example 11

To a 200 mL four-necked flask, TM-BIP-A (4.00 g, 0.011 mol, manufactured by Honshu Chemical Industry Co., Ltd., Formula (4-24)) and washed 15JWET (8.00 g, trade name Amberlist, manufactured by The Dow Chemical Company) as an ion-exchange resin catalyst were added and ethylene glycol isopropyl ether (80.00 g, manufactured by KANTO CHEMICAL CO., INC.) was charged. The mixture was stirred to start polymerization at 40° C. 22 hours later, the temperature of the mixture was raised to 70° C. to carry out the reaction for 12 hours. After the reacted mixture was left to cool, 15JWET was removed by filtration. The filtrate was concentrated at 30° C. under reduced pressure for 2 hours and dried to obtain 3.0 g of the target material (a compound corresponding to Formula (3-40) was a main product and compounds of Formula (3-37), Formula (3-38), and Formula (3-39) were mixed in the compound of Formula (3-40); hereinafter abbreviated as EGIPE-BIP-A).

Structure analysis was carried out with $^1$H-NMR to confirm that the target compound was obtained. The existence ratio of the tetra-substituted compound of EGIPE-BIP-A was confirmed to be 84 mol % in the whole EGIPE-BIP-A with HPLC.

Figure 9:
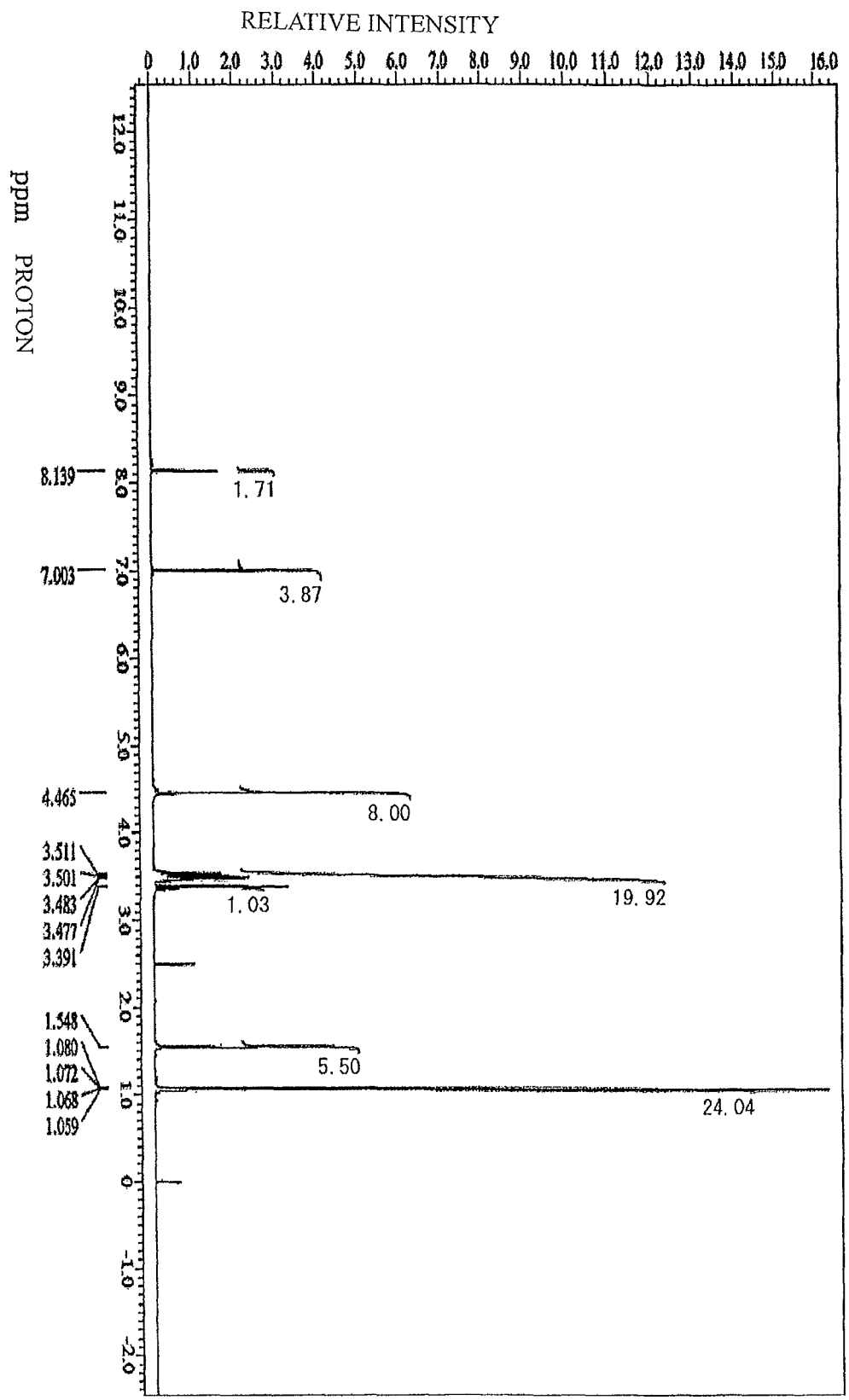
FIG. 9 is an NMR spectrum of the tetra-substituted compound of EGIPE-BIP-A obtained in Synthesis Example 11.

The NMR spectrum of the tetra-substituted compound of EGIPE-BIP-A showed the following characteristic absorptions (FIG. 9).

$^1$H-NMR (500 MHz, DMSO-d6): 1.07 ppm (t, 24H), 1.55 ppm (s, 6H), 3.45-3.57 ppm (m, 20H), 4.47 (s, 8H), 7.00 (s, 4H), 8.14 (s, 2H).

Synthesis Example 12

To a 100 mL four-necked flask, N-phenyl-1-naphthylamine (10.00 g, 0.046 mol, manufactured by Tokyo Chemical Industry Co., Ltd.), 1-naphthaldehyde (7.12 g, 0.046 mol, manufactured by Tokyo Chemical Industry Co., Ltd.), and Para-toluenesulfonic acid monohydrate (0.908 g, 0.0046 mol, manufactured by KANTO CHEMICAL CO., INC.) were added and 1,4-dioxane (21.03 g, manufactured by KANTO CHEMICAL CO., INC.) was charged, followed by stirring the mixture. The temperature of the mixture was raised to 110° C. to dissolve the mixture and to start polymerization. 12 hours later, the reaction product was left to cool down to room temperature and thereafter reprecipitated in methanol (400 g, KANTO CHEMICAL CO., INC.). The obtained precipitate was filtered and dried with a vacuum dryer at 50° C. for 10 hours and further at 120° C. for 24 hours to give 11.6 g of the target polymer (corresponding to Formula (5-1), hereinafter abbreviated as pNPNA-NA). The weight average molecular weight Mw of the pNPNA-NA measured with GPC in terms of polystyrene was 1,400 and the degree of multiple distribution Mw/Mn was 1.62.

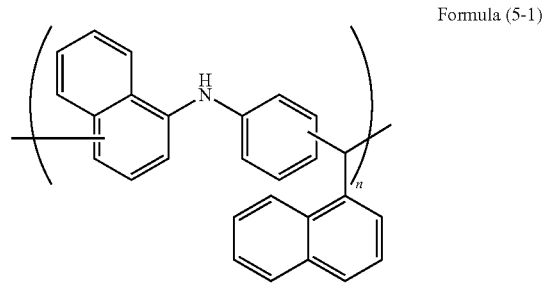

Formula (5-1)

Example 1

0.10 g of TMOM-BP-PGME in Synthesis Example 1 as a crosslinking agent, 0.02 g of pPTS (pyridinium para-toluenesulfonate) as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 μm and then further filtered with a polyethylene microfilter having a pore diameter of 0.05 μm to prepare a solution of a resist underlayer film-forming composition for use in a lithography process by a multilayer film.

Example 2

0.10 g of TMOM-BP-PGME2 in Synthesis Example 2 as a crosslinking agent, 0.02 g of pPTS as a catalyst, and 0.001

Example 3

0.10 g of TBOM-BP-BU in Synthesis Example 3 as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 μm and then further filtered with a polyethylene microfilter having a pore diameter of 0.05 μm to prepare a solution of a resist underlayer film-forming composition for use in a lithography process by a multilayer film.

Example 4

0.10 g of TBOM-BIP-A in Synthesis Example 4 as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 μm and then further filtered with a polyethylene microfilter having a pore diameter of 0.05 μm to prepare a solution of a resist underlayer film-forming composition for use in a lithography process by a multilayer film.

Example 5

0.10 g of TPOM-BIP-A in Synthesis Example 5 as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 μm and then further filtered with a polyethylene microfilter having a pore diameter of 0.05 μm to prepare a solution of a resist underlayer film-forming composition for use in a lithography process by a multilayer film.

Example 6

0.10 g of TEOM-BIP-A in Synthesis Example 6 as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 μm and then further filtered with a polyethylene microfilter having a pore diameter of 0.05 μm to prepare a solution of a resist underlayer film-forming composition for use in a lithography process by a multilayer film.

Example 7

0.10 g of TIBOM-BIP-A in Synthesis Example 7 as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 μm and then further filtered with a polyethylene microfilter having a pore diameter of 0.05 μm to prepare a solution of a resist underlayer film-forming composition for use in a lithography process by a multilayer film.

Example 8

0.10 g of EGME-BIP-A in Synthesis Example 8 as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 μm and then further filtered with a polyethylene microfilter having a pore diameter of 0.05 μm to prepare a solution of a resist underlayer film-forming composition for use in a lithography process by a multilayer film.

Example 9

0.10 g of EGEE-BIP-A in Synthesis Example 9 as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 μm and then further filtered with a polyethylene microfilter having a pore diameter of 0.05 μm to prepare a solution of a resist underlayer film-forming composition for use in a lithography process by a multilayer film.

Example 10

0.10 g of PGME-BIP-A in Synthesis Example 10 as a crosslinking agent, 0.02 g of pPTS as a catalyst, and 0,001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 µm and then further filtered with a polyethylene microfilter having a pore diameter of 0.05 µm to prepare a solution of a resist underlayer film-forming composition for use in a lithography process by a multilayer film.

Example 11

0.10 g of EGIPE-BIP-A in Synthesis Example 11 as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 µm and then further filtered with a polyethylene microfilter having a pore diameter of 0.05 µm to prepare a solution of a resist underlayer film-forming composition for use in a lithography process by a multilayer film.

Comparative Example 1

0.10 g of TMOM-BP (manufactured by Honshu Chemical Industry Co., Ltd., Formula (4-23)) as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 µm and then further filtered with a polyethylene microfilter having a pore diameter of 0.05 µm to prepare a solution of a resist underlayer film-forming composition for use in a lithography process by a multilayer film.

Comparative Example 2

0.10 g of TM-BIP-A (manufactured by Honshu Chemical Industry Co., Ltd., Formula (4-24)) as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 µm and then further filtered with a polyethylene microfilter having a pore diameter of 0.05 µm to prepare a solution of a resist underlayer film-forming composition for use in a lithography process by a multilayer film.

Comparative Example 3

0.10 g of tetramethoxymethyl glycoluril as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 µm and then further filtered with a polyethylene microfilter having a pore diameter of 0.05 µm to prepare a solution of a resist underlayer film-forming composition for use in a lithography process by a multilayer film.

Comparative Example 4

0.10 g of tetrabutoxymethyl glycoluril as a crosslinking agent, 0.02 g of pPTS as a catalyst, and 0.001 g of MEGAFAC R-30N (manufactured by Dainippon Ink and Chemicals Inc., trade name) as a surfactant were mixed with 0.51 g of pNPNA-NA resin obtained in Synthesis Example 12, and the mixture was dissolved in 7.16 g of PGMEA (propylene glycol monomethyl ether acetate), 1.52 g of PGME, and 2.39 g of cyclohexanone to prepare a solution. Thereafter, the solution was filtered with a polyethylene microfilter having a pore diameter of 0.10 µm and then further filtered with a polyethylene microfilter having a pore diameter of 0.05 µm to prepare a solution of a resist underlayer film-forming composition for use in a lithography process by a multilayer film.

(Measurement of Sublimate Amount)

The sublimate amount was measured with sublimate amount measurement apparatus described in WO 2007/111147 Pamphlet. First, each of the resist underlayer film-forming compositions prepared in Examples 1 to 11 and Comparative Examples 1 to 4 was applied onto a silicon wafer substrate having a diameter of 4 inch with a spin coater so that the film thickness was 100 nm. The wafer onto which the resist underlayer film was applied was placed in the sublimate amount measurement apparatus integrally equipped with a hot plate and baked for 120 seconds to collect the sublimate into a QCM (Quartz Crystal Microbalance) sensor, that is, a quartz oscillator on which electrodes were formed. The QCM sensor can measure a slight mass change by using a property that attachment of the sublimate to the surface (electrodes) of the quartz oscillator changes (decreases) the frequency of the quartz oscillator depending on the mass of the attached sublimate.

Detailed measurement procedure is as follows. The temperature of the hot plate in the sublimate amount measurement apparatus was raised to the measurement temperature listed in Table 1. A pump flow rate was set to 1 m$^3$/s and the apparatus was left to stand for the first 60 seconds for stabilizing the apparatus. Immediately thereafter, the wafer covered with the resist underlayer film was quickly placed on the hot plate through a sliding opening. The sublimate generated from 60 seconds to 180 seconds after the placement (during 120 seconds) was collected. The QCM sensor of the sublimate amount measurement apparatus and a flow attachment (detection part) connected to a collection funnel part were used without attaching nozzles. Consequently, air flow inflows without being narrowed from a channel (a bore diameter: 32 mm) of a chamber unit having a distance to the sensor (quartz oscillator) of 30 mm. As the QCM sensor, a material made of silicon and aluminum (AlSi) as main components for electrode was used and a QCM sensor having a diameter (sensor diameter) of the surface of the quartz oscillator of 14 mm, an electrode diameter of the surface of the quartz oscillator of 5 mm, and a resonance frequency of 9 MHz was used.

The obtained frequency change was converted to gram based on the specific value of the quartz oscillator for use in the measurement to clarify the relationship between the sublimate amount from one wafer onto which the resist underlayer film was applied and the time elapsed. Here, the initial 60 seconds was a period of time when the apparatus was left to stand for stabilizing the apparatus (the wafer was not placed). The measurement value measured at the point of time of 60 seconds to 180 seconds after placing the wafer on the hot plate is a measurement value of the sublimate amount from the wafer. The sublimate amounts of the resist underlayer films quantified with the apparatus are listed in Table 1 as sublimate amount ratios. The upper limit of the sublimate amount is determined to be 2,000 ng. The sublimate amount equal to or less than the upper limit is defined to be good, whereas the amount equal to or more than the upper limit is defined to be poor. The sublimate amount of 2,000 ng or less is listed as ◯ and the sublimate amount of 2,000 ng or more is listed as X.

TABLE 1

Sublimate amount generated from resist underlayer film

| Resist underlayer film | Baking temperature | Sublimate amount |
|---|---|---|
| Example 1 | 240° C. | ◯ |
| Example 2 | 240° C. | ◯ |
| Example 3 | 240° C. | ◯ |
| Example 4 | 240° C. | ◯ |
| Example 5 | 240° C. | ◯ |
| Example 6 | 240° C. | ◯ |
| Example 7 | 240° C. | ◯ |
| Example 8 | 240° C. | ◯ |
| Example 9 | 240° C. | ◯ |
| Example 10 | 240° C. | ◯ |
| Example 11 | 240° C. | ◯ |
| Comparative Example 1 | 240° C. | X |
| Comparative Example 2 | 240° C. | ◯ |
| Comparative Example 3 | 240° C. | ◯ |
| Comparative Example 4 | 240° C. | ◯ |

(Elution Test to Photoresist Solvent)

Each of the resist underlayer film-forming composition solutions prepared in Examples 1 to 11 and Comparative Examples 1 to 4 was applied onto a silicon wafer with a spin coater. The applied solution was baked on a hot plate at 400° C. for 2 minutes to form a resist underlayer film (film thickness 0.25 The resist underlayer film was immersed into solvents for use in the resist, for example, ethyl lactate, propylene glycol monomethyl ether, propylene glycol monomethyl ether acetate, and cyclohexanone. It was confirmed that the resist underlayer film was insoluble to these solvents.

(Embeddability Test to Hole Pattern)

Whether the resist underlayer film-forming composition can be embedded well in the hole was evaluated. The resist underlayer film-forming substance was applied with a spin coater onto a tetraethylorthosilicate (TEOS) substrate in which holes (hole diameter: 0.120 nm, pitch: a ratio of hole diameter/space between holes=1/0.8, hole depth: 400 nm) were formed. Thereafter, the applied film was heated on the hot plate at 240° C. for 1 minute to form a resist underlayer film (in the case of application of gap fill material for lithography) having a thickness of about 120 nm. The embeddability was evaluated by observing the sectional shapes of the TEOS substrates having holes to which the resist underlayer film-forming substances obtained in Examples 1 to 11 and Comparative Example 1 to 4 were applied using a scanning electron microscope (SEM). The case that the resist underlayer film was formed in the holes without clearance gaps was determined to be good ("◯"), whereas the case that the resist underlayer film was not embedded in the holes or openings or clearance gaps existed in the holes was determined to be poor ("X").

TABLE 2

Embeddability of resist underlayer film

| Resist underlayer film | Baking temperature | Embeddability |
|---|---|---|
| Example 1 | 240° C. | ◯ |
| Example 2 | 240° C. | ◯ |
| Example 3 | 240° C. | ◯ |
| Example 4 | 240° C. | ◯ |
| Example 5 | 240° C. | ◯ |
| Example 6 | 240° C. | ◯ |
| Example 7 | 240° C. | ◯ |
| Example 8 | 240° C. | ◯ |
| Example 9 | 240° C. | ◯ |
| Example 10 | 240° C. | ◯ |
| Example 11 | 240° C. | ◯ |
| Comparative Example 1 | 240° C. | ◯ |
| Comparative Example 2 | 240° C. | X |
| Comparative Example 3 | 240° C. | X |
| Comparative Example 4 | 240° C. | X |

INDUSTRIAL APPLICABILITY

Different from conventional materials having difficulty in satisfying both reduction in sublimate generation and embeddability in the hole pattern, the resist underlayer film-forming composition using the crosslinking agent of the present invention and for use in lithography processes can provide the resist underlayer film capable of having both properties.

The invention claimed is:

1. A resist underlayer film obtained by applying a resist underlayer film-forming composition onto a semiconductor substrate and baking the applied resist underlayer film-forming composition, the resist underlayer film-forming composition comprising:

a resin; and a crosslinkable compound of Formula (1) or Formula (2):

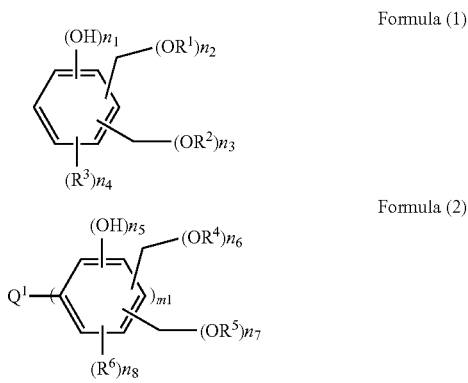

wherein $Q^1$ is a single bond or an m1-valent organic group; $R^1$ and $R^4$ are each a $C_{2-10}$ alkyl group having a $C_{1-10}$ alkoxy group; $R^2$ and $R^5$ are each a hydrogen atom or a methyl group; $R^3$ and $R^6$ are each a $C_{1-10}$ alkyl group or a $C_{6-40}$ aryl group;

n1 is an integer of 1≤n1≤3; n2 is an integer of 2 n2≤5; n3 is an integer of 0≤n3≤3; n4 is an integer of 0≤n4≤3; a total of the integers is an integer of 3≤(n1+n2+n3+n4)≤ 6; and n5 is an integer of 1≤n5≤3; n6 is an integer of 1≤n6≤4; n7 is an integer of 0≤n7≤3; n8 is an integer of 0≤n8≤3; a total of the integers is an integer of 2≤(n5+n6+n7+n8)≤ 5; and m1 is an integer of 2 to 10.

2. A method for forming a resist pattern for use in semiconductor production, the method comprising: applying a resist underlayer film-forming composition onto a semiconductor substrate, and baking the applied resist underlayer film forming composition to form a resist underlayer film, the resist underlayer film-forming composition comprising:
   a resin; and
   a crosslinkable compound of Formula (1) or Formula (2):

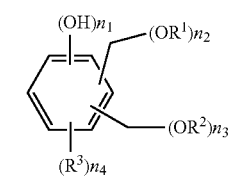

Formula (1)

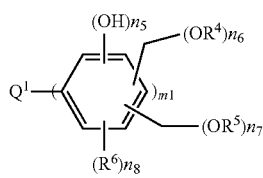

Formula (2)

wherein $Q^1$ is a single bond or an m1-valent organic group; $R^1$ and $R^4$ are each a $C_{2-10}$ alkyl group having a $C_{1-10}$ alkoxy group; $R^2$ and $R^5$ are each a hydrogen atom or a methyl group; $R^3$ and $R^6$ are each a $C_{1-10}$ alkyl group or a $C_{6-40}$ aryl group;

n1 is an integer of 1≤n1≤3; n2 is an integer of 2 n2≤5; n3 is an integer of 0≤n3≤3; n4 is an integer of 0≤n4≤3; a total of the integers is an integer of 3≤(n1+n2+n3+n4)≤ 6; and n5 is an integer of 1≤n5≤3; n6 is an integer of 1≤n6≤4; n7 is an integer of 0≤n7≤3; n8 is an integer of 0≤n8≤3; a total of the integers is an integer of 2≤(n5+n6+n7+n8)≤ 5; and m1 is an integer of 2 to 10.

3. A method for producing a semiconductor device, the method comprising:
   forming a resist underlayer film by applying a resist underlayer film-forming composition onto a semiconductor substrate, the resist underlayer film-forming composition comprising:
   a resin; and
   a crosslinkable compound of Formula (1) or Formula (2):

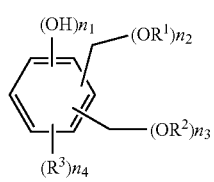

Formula (1)

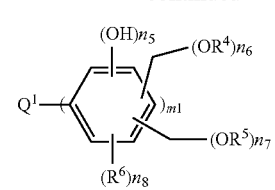

Formula (2)

wherein $Q^1$ is a single bond or an m1-valent organic group; $R^1$ and $R^4$ are each a $C_{2-10}$ alkyl group having a $C_{1-10}$ alkoxy group; $R^2$ and $R^5$ are each a hydrogen atom or a methyl group; $R^3$ and $R^6$ are each a $C_{1-10}$ alkyl group or a $C_{6-40}$ aryl group;

n1 is an integer of 1≤n1≤3; n2 is an integer of 2 n2≤5; n3 is an integer of 0≤n3≤3; n4 is an integer of 0≤n4≤3; a total of the integers is an integer of 3≤(n1+n2+n3+n4)≤ 6; and n5 is an integer of 1≤n5≤3; n6 is an integer of 1≤n6≤4; n7 is an integer of 0≤n7≤3; n8 is an integer of 0≤n8≤3; a total of the integers is an integer of 2≤(n5+n6+n7+n8)≤ 5; and m1 is an integer of 2 to 10;

forming a resist film on the resist underlayer film;
forming a resist pattern by irradiation with light or electron beams and development;
etching the resist underlayer film by using the formed resist pattern; and
processing the semiconductor substrate by using the patterned resist underlayer film.

4. A method for producing a semiconductor device, the method comprising:
   forming a resist underlayer film by applying a resist underlayer film-forming composition onto a semiconductor substrate, the resist underlayer film-forming composition comprising:
   a resin; and
   a crosslinkable compound of Formula (1) or Formula (2):

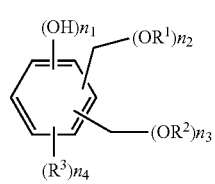

Formula (1)

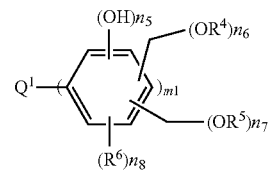

Formula (2)

wherein $Q^1$ is a single bond or an m1-valent organic group; $R^1$ and $R^4$ are each a $C_{2-10}$ alkyl group having a $C_{1-10}$ alkoxy group; $R^2$ and $R^5$ are each a hydrogen atom or a methyl group; $R^3$ and $R^6$ are each a $C_{1-10}$ alkyl group or a $C_{6-40}$ aryl group;

n1 is an integer of 1≤n1≤3; n2 is an integer of 2 n2≤5; n3 is an integer of 0≤n3≤3; n4 is an integer of 0≤n4≤3; a total of the integers is an integer of 3≤(n1+n2+n3+n4)≤ 6; and n5 is an integer of 1≤n5≤3; n6 is an integer of 1≤n6≤4; n7 is an integer of 0≤n7≤3; n8 is an integer of 0≤n8≤3; a total of the integers is an integer of 2≤(n5+n6+n7+n8)≤ 5; and m1 is an integer of 2 to 10;

forming a hard mask on the resist underlayer film;

forming a resist film on the hard mask;

forming a resist pattern by irradiation with light or electron beams and development;

etching the hard mask by using the formed resist pattern;

etching the resist underlayer film by using the patterned hard mask; and processing the semiconductor substrate by using the patterned resist underlayer film.

5. The method according to claim 4, wherein the hard mask is formed by application of an inorganic substance or vapor-deposition of an inorganic substance.

6. A compound of Formula (5):

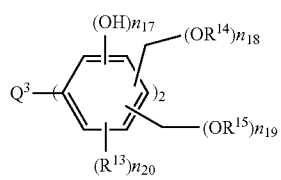

Formula (5)

wherein $Q^3$ is an isopropylidene group; $R^{14}$ is a $C_{2-10}$ alkyl group having a $C_{1-10}$ alkoxy group; $R^{15}$ is a hydrogen atom or a methyl group; $R^{13}$ is a $C_{1-10}$ alkyl group or a $C_{6-40}$ aryl group;

n17 is an integer of 1≤n17≤3; n18 is an integer of 1≤n18≤4; n19 is an integer of 0≤n19≤3; n20 is an integer of 0≤n20≤3; and a total of the integers is an integer of 2≤(n17+n18+n19+n20)≤5.

7. A composition comprising at least one of a compound of Formula 3-33, Formula 3-34, Formula 3-35, or Formula 3-36:

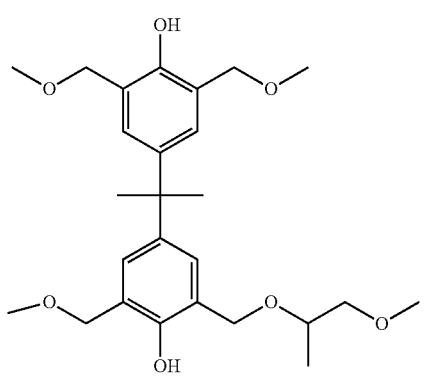

Formula (3-33)

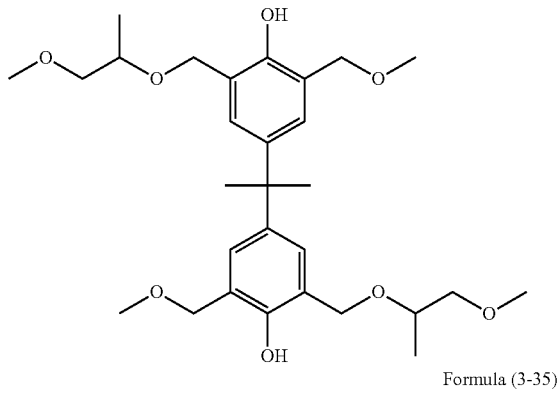

Formula (3-34)

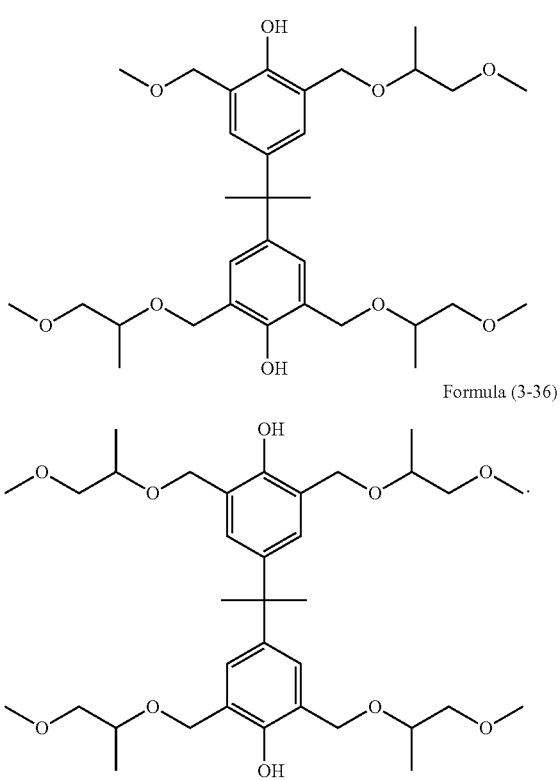

Formula (3-35)

Formula (3-36)

8. The composition according to claim 7, where in the composition comprises a compound of Formula 3-33.

9. The composition according to claim 7, where in the composition comprises a compound of Formula 3-34.

10. The composition according to claim 7, where in the composition comprises a compound of Formula 3-35.

11. The composition according to claim 7, where in the composition comprises a compound of Formula 3-36.

12. The composition according to claim 7, where in the composition comprises a compound of Formula 3-33, Formula 3-34, Formula 3-35, and Formula 3-36.

* * * * *